(12) United States Patent
Weiser

(10) Patent No.: US 8,033,982 B2
(45) Date of Patent: Oct. 11, 2011

(54) SYSTEMS, DEVICES AND METHODS RELATING TO A SHAPE RESILIENT SLING-LIKE SUPPORT FOR TREATING URINARY INCONTINENCE

(75) Inventor: Michael F. Weiser, Groton, MA (US)

(73) Assignee: Boston Scientific Scimed, Inc., Boston, MA (US)

(*) Notice: Subject to any disclaimer, the term of this patent is extended or adjusted under 35 U.S.C. 154(b) by 1179 days.

(21) Appl. No.: 11/197,421

(22) Filed: Aug. 3, 2005

(65) Prior Publication Data

US 2007/0032695 A1 Feb. 8, 2007

(51) Int. Cl.
*A61F 2/02* (2006.01)

(52) U.S. Cl. .............. 600/30; 600/37; 128/DIG. 25

(58) Field of Classification Search ............ 600/29–32, 600/37; 602/4, 6–11; 606/191–200; 623/11.11–13.18, 16.11–17.13, 23.64–23.66; 128/885, 889, DIG. 25, 897, 899; 267/36.1–37.2, 267/42–45, 47, 67
See application file for complete search history.

(56) References Cited

U.S. PATENT DOCUMENTS

| | | | |
|---|---|---|---|
| 5,195,542 A | 3/1993 | Gazielly et al. | |
| 5,368,602 A | 11/1994 | de la Torre | |
| 5,500,000 A | 3/1996 | Feagin et al. | |
| 5,641,566 A | 6/1997 | Kranzler et al. | |
| 5,824,082 A | 10/1998 | Brown | |
| 5,922,026 A | 7/1999 | Chin | |
| 6,042,534 A | 3/2000 | Gellman et al. | |
| 6,110,101 A | 8/2000 | Tihon et al. | |
| 6,491,703 B1 | 12/2002 | Ulmsten | |
| 6,500,194 B2 | 12/2002 | Benderev et al. | |
| 6,506,190 B1 | 1/2003 | Walshe | |
| 6,575,987 B2 | 6/2003 | Gellman et al. | |
| 6,592,515 B2 | 7/2003 | Thierfelder et al. | |
| 6,592,610 B2 | 7/2003 | Beyar | |
| 6,648,921 B2 | 11/2003 | Anderson et al. | |
| 6,666,817 B2 | 12/2003 | Li | |
| 6,730,110 B1 | 5/2004 | Harari et al. | |
| 6,736,823 B2 | 5/2004 | Darois et al. | |
| 6,755,781 B2 | 6/2004 | Gellman | |
| 2002/0138025 A1 | 9/2002 | Gellman et al. | |
| 2002/0161382 A1 | 10/2002 | Heisz et al. | |
| 2002/0183588 A1* | 12/2002 | Fierro ........................... 600/30 |
| 2002/0188169 A1 | 12/2002 | Kammerer et al. | |
| 2003/0216743 A1 | 11/2003 | Hoffman | |
| 2004/0006353 A1 | 1/2004 | Bosley, Jr. et al. | |
| 2004/0039246 A1 | 2/2004 | Gellman et al. | |
| 2004/0106847 A1 | 6/2004 | Benderev | |
| 2004/0143152 A1 | 7/2004 | Grocela | |
| 2004/0144395 A1 | 7/2004 | Evans et al. | |
| 2004/0225181 A1 | 11/2004 | Chu et al. | |
| 2004/0231678 A1 | 11/2004 | Fierro | |
| 2005/0038452 A1 | 2/2005 | Chu | |

FOREIGN PATENT DOCUMENTS

| | | | |
|---|---|---|---|
| EP | 0 677 297 B1 | | 12/2000 |
| WO | WO 98/35632 | * | 8/1998 |
| WO | WO 00/74594 A1 | | 12/2000 |
| WO | WO 02/19945 A2 | | 3/2002 |
| WO | WO 02/30293 A1 | | 4/2002 |
| WO | WO 03/007847 A1 | | 1/2003 |

(Continued)

*Primary Examiner* — Charles A Marmor, II
*Assistant Examiner* — Carrie R Dorna
(74) *Attorney, Agent, or Firm* — Bingham McCutchen LLP

(57) ABSTRACT

The invention, in one embodiment, is directed to systems, devices and methods for supporting an anatomical location using a self-supporting implantable device without a need for an anchor.

17 Claims, 11 Drawing Sheets

FOREIGN PATENT DOCUMENTS

| WO | WO-03/086205 A2 | 10/2003 |
| WO | WO 2004/004600 A1 | 1/2004 |
| WO | WO 2004/067056 | 7/2004 |
| WO | WO-2004/096088 A2 | 11/2004 |
| WO | WO-2005/048850 A2 | 6/2005 |
| WO | WO-2005/112819 A1 | 12/2005 |

* cited by examiner

SYSTEMS, DEVICES AND METHODS RELATING TO A SHAPE RESILIENT SLING-LIKE SUPPORT FOR TREATING URINARY INCONTINENCE

FIELD OF THE INVENTION

The invention generally relates to surgically implantable devices for treating urinary incontinence. More specifically, in various embodiments, the invention is directed to systems, devices and methods relating to a surgically implantable shape resilient sling-like support for providing a urethral platform.

BACKGROUND

Urinary incontinence affects over 13 million men and women of all ages in the United States. Stress urinary incontinence (SUI) affects primarily women and is generally caused by two conditions, intrinsic sphincter deficiency (ISD) and hypermobility. These conditions may occur independently or in combination. In ISD, the urinary sphincter valve, located within the urethra, fails to close properly (coapt), causing urine to leak out of the urethra during stressful activity. Hypermobility is a condition in which the pelvic floor is distended, weakened, or damaged, causing the bladder neck and proximal urethra to rotate and descend in response to increases in intra-abdominal pressure (e.g., due to sneezing, coughing, straining, etc.). The result is that there is an insufficient response time to promote urethral closure and, consequently, urine leakage and/or flow results.

A popular treatment of SUI is the use of a sling, which is permanently placed under a patient's bladder neck or mid-urethra to provide a urethral platform. Placement of the sling limits the endopelvic fascia drop, while providing compression to the urethral sphincter to improve coaptation. Generally, the sling is surgically placed under urethra, close to the high-pressure zone with no elevation of the urethra. The ends of a sling may be secured to an anatomical location by, for example, a bone anchor. When abdominal pressure increases, the sling stops the descent of the urethra and functions as a mechanism of closure for the urethra to prevent urine leakage by maintaining its position relative to the anchored location. However, too much tension may be applied by this method, and the patient may go into retention, unable to void the bladder and suffer a pressure build-up in the bladder. Such pressure build-up can lead to reflux of urine up the ureters and into the kidney, eventually resulting in kidney damage, and, potentially, kidney loss. Clinically, there is technical challenge to positioning and applying the correct tension to the sling.

Additionally, conventional slings are typically formed from a woven fabric. The woven fabric can become twisted, stretched or otherwise permanently deformed during implantation, which can affect whether the sling operates correctly. To address this issue, conventional slings typically employ a protective sleeve to reduce the likelihood of the sling becoming deformed during implantation. A disadvantage of this configuration is that the sleeve ultimately needs to be removed from the patient's body.

Accordingly, there is a need for an improved surgically implantable sling-like support to which it is easier to apply a correct tension, and that does not easily permanently deform and/or require a protective covering.

SUMMARY OF THE INVENTION

The invention addresses the deficiencies in the prior art by, in various embodiments, providing systems, devices and methods relating to a shape resilient sling-like support for treating urinary incontinence. In one aspect, the invention provides a sling-like device formed from a shape resilient material. According to one embodiment, the sling-like device has an original size and shape for providing support to a patient's urethra or bladder neck. In response to a mechanical force, the sling-like device can flex, bend or otherwise non-destructively and reversibly deform, in effect, to become spring loaded. In response to the force being removed, the sling-like device returns to it's original shape. In one configuration, the sling-like device is flexible enough to bend, fold or otherwise deform, for example, during an implantation procedure, and has sufficient shape resilience to return to its original shape once implanted.

According to another feature, the tensioning of the sling-like device is self adjusting in that it may flex/bend, for example, in response to a patient's muscles contracting or expanding, in response to movement by a patient, and/or in response to changes in a patient's anatomy. Such flexibility provides increased comfort for a patient and also reduces the likelihood of over or under tensioning. Such shape resiliency also enables the sling-like device to expand and compress to provide a more constant level of support to the urethra.

The device may be formed from any biocompatible material that provides a degree of rigidity with spring-like resilience, such as a shape memory alloy, which may be polymer or metal composite. The device of the invention can be made, for example, of a synthetic material such as nylon, polyethylene, polyester, polypropylene, fluoropolymers or a co-polymer thereof, or of a mammalian tissue material such as bovine, porcine, equine, human cadaveric or engineered tissue. In one embodiment, the material of the device includes a combination of synthetic and mammalian tissue materials. According to some embodiments, the device of the invention includes one or more sections that are biodegradable and/or bioabsorbable. According to other embodiments, the entire device is biodegradable and/or bioabsorbable. In one configuration, the device dissolves subsequent to scar tissue or other supportive tissue structure developing around the device.

According to a further embodiment, the device includes a mechanism for associating it with a delivery device. By way of example, the device may include a through aperture, a dilator tube, a loop, a hollow closed end fitting, or other suitable mechanism for coupling to a distal end of a delivery device during implantation. According to another configuration, the delivery device is a medical operator's hand, and the association mechanism includes a structure for receiving, for example, the tip of a finger of the medical operator.

In some embodiments, the sling-like device is held in place by the tissue surrounding the device, and need not be anchored to a bone or soft tissue. However, according to other embodiments, the ends of the sling-like device may be anchored in any suitable fashion, including without limitation, using soft tissue or bone anchors, or sutures. In one configuration, the sling-like device includes one or more surface irregularities for assisting in holding the support at an anatomical location. The surface irregularities may be provided by, for example, one or more ridges, projections, pores, protrusions, depressions or a combination thereof. In one configuration, the surface irregularities are located at each end of the support, are directional in nature and are sized and shaped for allowing the device to be inserted into a patent's tissues and for engaging with a patient's tissues to resist the sling from being removed from the patient.

The device of the invention may be treated with any suitable agent, including a protective, therapeutic or lubricious agent. According to one embodiment, the device is treated with a pharmaceutical agent, which may, for example, include an antibiotic, anti-inflammatory, growth factor, hormone, and/or other suitable biological and/or chemical agent for aiding in tissue repair or prevention of complication from surgical procedures. The growth factors and/or hormones may be, for example, such that promote formation of scar tissue. Preferably, such tissue stabilizes and anchors the device, and helps ameliorate urinary incontinence. Although not necessary, the device may be used with a sleeve for covering at least a portion of it during implantation process. The sleeve may be treated with an agent, such as those described above, and may be biodegradable/bioabsorbable.

In another aspect, the invention provides a method of treating urinary incontinence, including the steps of surgically making an incision in the vaginal wall of a patient in lower proximity of the urethra or bladder neck, and delivering the device to the periurethral tissue of a patient to provide a flexible, shape resilient support under the urethra.

In a further aspect, the invention provides a system for treating urinary incontinence, the system including a support assembly and a delivery device. The support assembly includes a semi-rigid, shape resilient elongated support sized and shaped for placement under the urethra or bladder neck in the periurethral tissue of a patient. The support assembly also includes a mechanical feature, such as, without limitation, an aperture, loop, dilator tube, hollow anchor or other suitable feature for engaging with a distal end of a delivery device. According to one embodiment, the delivery device includes a handle, a shaft extending distally from the handle, and a pusher assembly interfitted over the shaft. The distal end of the shaft is sized and shaped to engage with the particular sling end feature. A medical operator slides the pusher assembly distally along the shaft to disengage the sling end from the distal end of the delivery device once the sling end is placed in a desired location.

Other features of the invention will be apparent from the following description of illustrative embodiments.

BRIEF DESCRIPTION OF THE DRAWINGS

The following figures depict certain illustrative embodiments of the invention in which like reference numerals refer to like elements. These depicted embodiments may not be drawn to scale and are to be understood as illustrative of the invention and not as limiting in any way.

DESCRIPTION OF ILLUSTRATIVE EMBODIMENTS

As described above in summary, the invention in various embodiments is directed to systems, methods, devices and assemblies relating to a shape resilient sling-like support for treating urinary incontinence.

Figure 1:
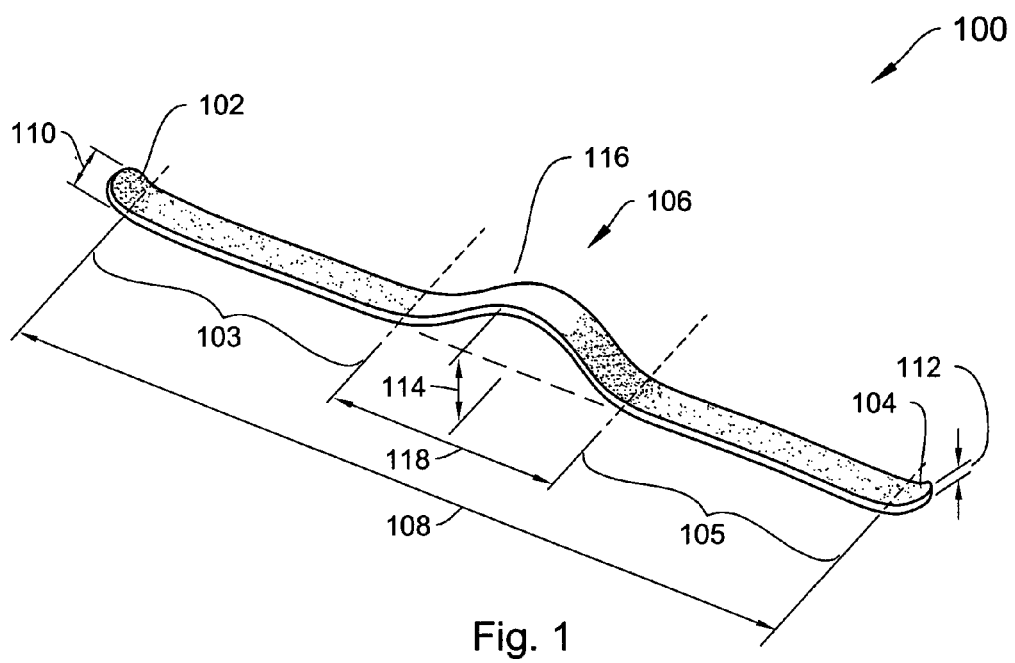
FIG. 1 depicts a top perspective view of a sling-like supportive device formed from a shape-resilient material and having an intermediate portion that is curved upward for supporting an anatomical location according to an illustrative embodiment of the invention.

FIG. 1 depicts a top perspective view of a sling-like supportive device 100 formed from a shape-resilient material according to an illustrative embodiment of the invention. According to the illustrative embodiment, the device 100 includes first 102 and second 104 ends and an intermediate portion 106 located between the first 102 and second 104 ends. The device 100 also includes a first axially peripheral section 103 extending between the first end 102 and the intermediate portion 106, and a second axially peripheral section 105 extending between the intermediate portion 106 and the second end 104. According to one illustrative configuration, the device 100 has a length 108 of about 2 cm to about 15 cm, and a width 110 of about 0.5 cm to about 2.5 cm. The illustrative device 100 has a thickness 112 of about 0.5 mm to about 3 mm. According to other illustrative embodiments, the length 108 is about 2 cm to about 6 cm, and may be about 3.5 cm to about 4.5 cm.

Under rest conditions, the axially peripheral sections 103 and 105 are located substantially coplanar with each other. The intermediate portion 106 curves upward out of the plane of the of the sections 103 and 105 to a height 114 of about 0.2 cm to about 5 cm. In some configurations, the height 114 is about 1 cm to about 4 cm or about 2 cm to about 3 cm. The ends 102 and 104 also bend upward out of the rest plane of the sections 103 and 105. According to the illustrative embodiment, the sling-like support 100 is sized and shaped for implantation into the periurethral tissues of a patient to provide a urethral platform. As such, any suitable dimensions may be employed.

Also, although the device 100 is shown as being elongate in nature, this need not be the case, as it may have any suitable shape for providing support to the particular anatomical location being supported. By way of example, the device 100 may be rectangular or substantially rectangular, trapezoidal, hexagonal, octagonal or elliptical in shape, as may be suitable for its intended location at a particular anatomical site. The edges of the device 100 may be linear in nature (e.g., relatively smooth and not tanged) or may have V-shaped projections or be frayed (e.g., tanged) at the edge. In some illustrative embodiments, the device 100 includes apertures, of any suitable shape and size, for example, round, square, diamond-shaped, or triangular. In other illustrative embodiments, at least one of the sides of the device 100 is textured. The textured or irregular surface acts to enhance tissue growth into the device 100 and also aids in stabilization of the device 100 in the tissue through frictional forces. In certain embodiments, part or all of one or both sides of the device 100 is textured, having a rough, grainy texture. In certain embodiments, one or both sides of the device 100 have distinct structures to act as fixation points such as shown as illustrative examples in FIGS. 10A, 10B, and 10C, and described in more details below, to anchor the device within a tissue.

According to the illustrative embodiment of FIG. 1, the device 100 may be formed from any suitable biocompatible shape retaining material, and is constructed in a manner such that the device has an initial shape, for example, such as shown in the various illustrative embodiments. When implanted, a mid location 116 is aligned under the anatomical site to be supported. In response to forces created, for example, from patient movement, muscle flexing, and/or anatomical size changes, the device 100 may flex. By way of example, in response to a downward force on the intermediate portion 106, the height 114 may compress and extend the length 118 of the intermediate portion 106 and the overall length 108 of the device 100. The flexible give in the height 114 enables the intermediate portion 106 to exert a more constant upward force on the anatomical site being supported than would be the case if the intermediate portion 106 was rigid or otherwise tensioned to such a degree as not to allow similar give. In response to the force being removed, the shape resilience of the device material causes both the height 114 and the lengths 108 and 118 to return to their initial values.

In a similar fashion, an upward or downward force applied to the end 102 and/or the end 104 causes the respective end to deflect downward or upward, depending on the direction of the force. However, because the sections 103 and/or 105 also flex, the forces applied to the ends 102 and 104 have a reduced, if any, effect on the supportive pressure applied upward to the anatomical site by the intermediate portion 106.

Figure 14A:
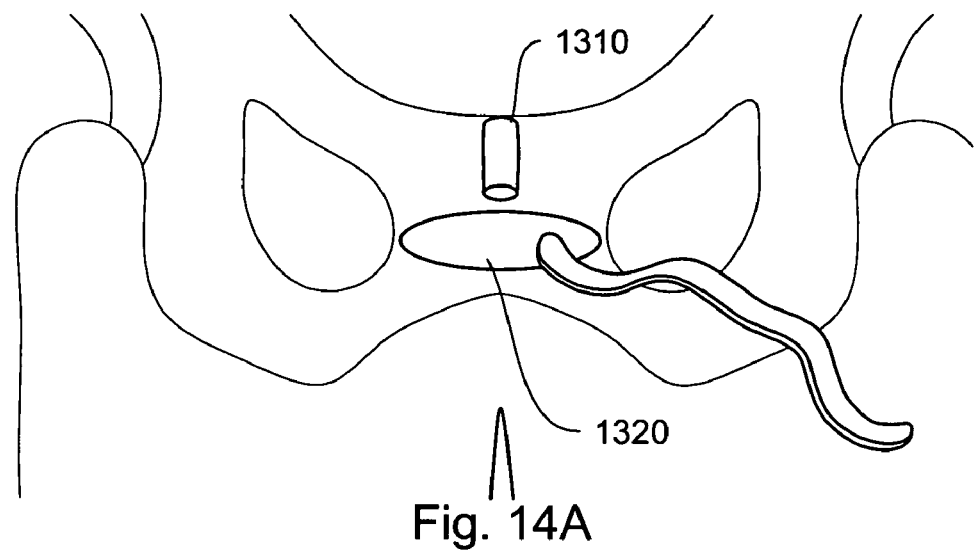
FIGS. 14A-14C illustrate a procedure for implanting a sling-like supportive device of the type depicted in FIG. 1 into the body of a patient according to an illustrative embodiment of the invention.
Figure 14B:
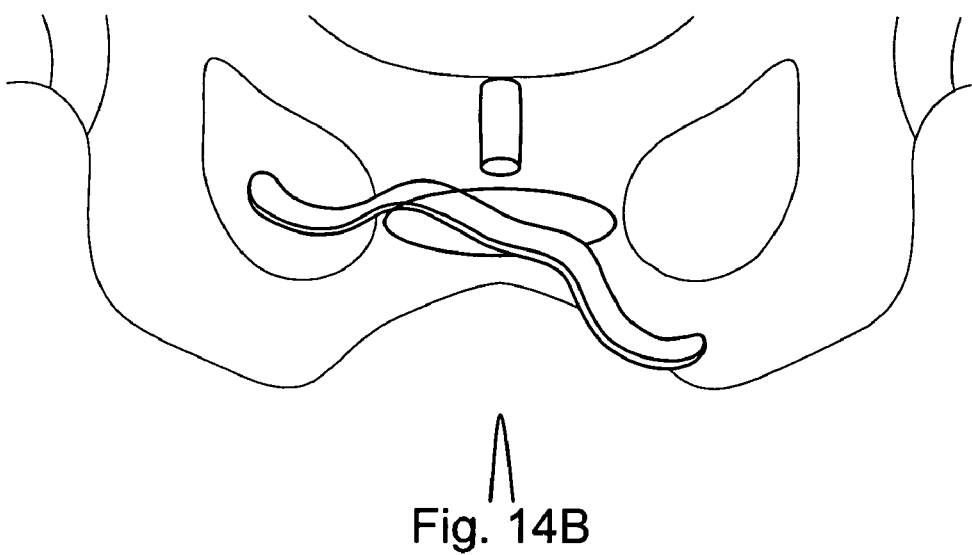
Figure 14C:
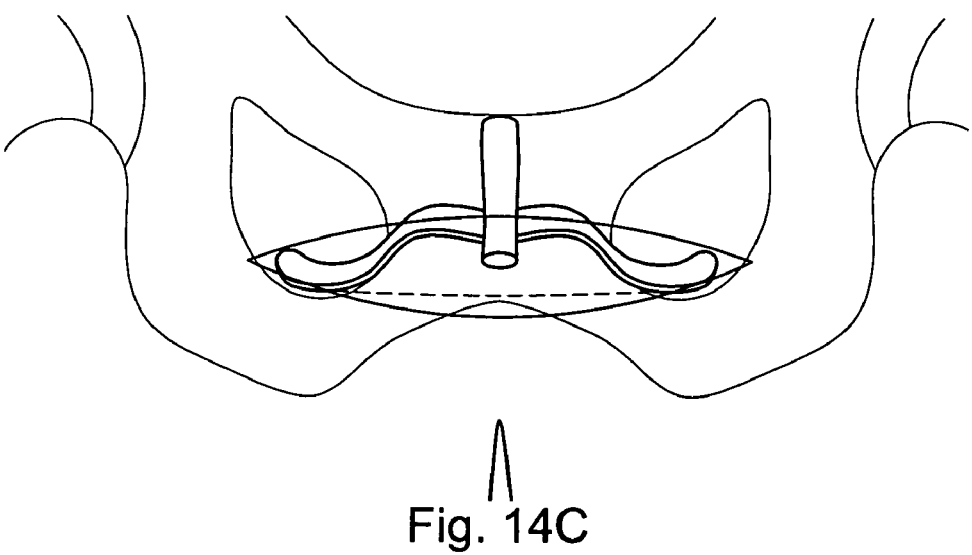

As described below in more detail with respect to FIGS. 14A-14C, the device 100 may be folded, bent or otherwise compressed when surgically placed at the anatomical site to be supported. The spring-loaded/shape-resilient features of the device 100 cause it to return to a preset shape subsequent to implantation to provide the appropriate support. According to various configurations, the device 100 may be constructed from any suitable biocompatible polymer, shape-memory alloy or composite polymer with varying tensile strengths and/or stiffness for various parts of the device. For example, the axially intermediate portion 106 may be manufactured from materials with less stiffness than the axially peripheral sections 103 and 105, and/or the device ends 102 and 104. The device 100 may be made, for example, of a synthetic material such as nylon, polyethylene, polyester, polypropylene, fluoropolymers or a co-polymer thereof, or for example, of a mammalian tissue material such as bovine, porcine, equine, human cadaveric or engineered tissue. In some illustrative embodiments, the material of the device includes a combination of synthetic and mammalian tissue materials.

The supportive device 100 may be treated with any suitable material. For example, in some illustrative embodiments, the device 100 includes a protective sleeve or treatment. Exemplary bioabsorbable/dissolvable materials from which the protective treatment may be made include, but are not limited to, alginates, sugar based formulations, starches, gelatins, cellulose, polyvinyl alcohol, polyglycolic acid (PGA), polylactic acid (PLA), polydioxinone (PDO), and/or other synthetic or natural polymers including combinations thereof. The biocompatible protective treatment may cover any portion or all of the device 100. In one particular configuration, the protective treatment encapsulates or substantially encapsulates at least portion of the device 100. According to one feature, the protective treatment is formed from lubricious material and reduces the friction between the device 100 and the patient's periurethral tissues. In this way, the protective treatment can provide a relatively smooth tissue contact surface to otherwise tanged or ragged device edges to reduce the likelihood of the device 100 irritating the patient's tissues during implantation.

The protective treatment may be applied to the device 100 by any suitable approach, for example, by way of spraying, brushing or dipping the portion of the device 100 to be treated. According to another illustrative embodiment, the protective treatment is formed as a sheet of material that can be affixed to the portion of the device 100 to be treated. According to another feature, the treatment may be configured to dissolve within a particular time range. The treatment may be configured, for example, to substantially absorb into the patient's tissues within about 30, 15, 10 or 5 minutes from the time the sling is implanted. Alternatively, the treatment may be configured to substantially absorb into the patient's tissues over a time span of hours, days, weeks, or months.

According to another feature, at least a portion of the device 100 is biodegradable and may also dissolve and/or be absorbed into the patient's tissues. For example, in some illustrative embodiments, only a section of the device 100, such as, for example, the intermediate portion 106, is biodegradable. Exemplary biodegradable materials, in addition to those listed above, which may be employed for the device 100 include, but are not limited to, polylactic acid, polyglycolic acid and copolymers and mixtures thereof, such as poly(L-lactide) (PLLA), poly(D,L-lactide) (PLA), polyglycolic acid [polyglycolide (PGA)], poly(L-lactide-co-D, L-lactide) (PLLA/PLA), poly(L-lactide-co-glycolide) (PLLA/PGA), poly(D,L-lactide-co-glycolide) (PLA/PGA), poly(glycolide-co-trimethylene carbonate) (PGA/PTMC), poly( D,L-lactide-co-caprolactone) (PLA/PCL), and poly(glycolide-co-caprolactone) (PGA/PCL); polyethylene oxide (PEO); polydioxanone (PDS); polypropylene fumarate; polydepsipeptides, poly(ethyl glutamate-co-glutamic acid), poly (tert-butyloxy-carbonylmethyl glutamate); polycaprolactone (PCL), poly(hydroxy butyrate), polycaprolactone co-butylacrylate, polyhydroxybutyrate (PHBT) and copolymers of polyhydroxybutyrate; polyphosphazenes, poly(phosphate ester); maleic anhydride copolymers, polyiminocarbonates, poly[(97.5% dimethyl-trimethylene carbonate)-co-(2.5% trimethylene carbonate)], cyanoacrylate, hydroxypropylmethylcellulose; polysaccharides, such as hyaluronic acid, chitosan and regenerate cellulose; poly(amino acid) and proteins, such as gelatin and collagen; and mixtures and copolymers thereof.

According to another illustrative feature, the device 100 may also include an agent for release into the patient's tissues. One illustrative agent promotes, when applied to the patient's tissues in a pharmaceutically acceptable amount, well-organized collagenous tissue growth, such as scar tissue growth, preferably, in large quantities. According to one feature, the agent may or may not block or delay the dissolvability of the protective treatment. This may be controlled by selecting differing methods for loading the agent onto the device 100. The tissue growth factor may include natural and/or recombinant proteins for stimulating a tissue response so that collagenous tissue such as scar tissue growth is enhanced. Exemplary growth factors that may be used include, but are not limited to, platelet-derived growth factor (PDGF), fibroblast growth factor (FGF), transforming growth factor-beta (TGF-beta), vascular endothelium growth factor (VEGF), activin/TGF and sex steroid, bone marrow growth factor, growth hormone, insulin-like growth factor 1 and combinations thereof. The agent may also include a hormone, including but not limited to estrogen, steroid hormones, and other hormones to promote growth of appropriate collagenous tissue such as scar tissue. The agent may also include stem cells or other suitable cells derived from the host patient. These cells may be fibroblast, myoblast, or other progenitor cells to mature into appropriate tissues.

In various illustrative embodiments, the agent may include one or more therapeutic agents. The therapeutic agents may be, for example, anti-inflammatory agents, including steroidal and non-steroidal anti-inflammatory agents, analgesic agents, including narcotic and non-narcotic analgesics, local anesthetic agents, antispasmodic agents, growth factors, gene-based therapeutic agents, and combinations thereof.

Exemplary steroidal anti-inflammatory therapeutic agents (glucocorticoids) include, but are not limited to, 21-acetoxyprefnenolone, alclometasone, algestone, amicinonide, beclomethasone, betamethasone, budesonide, chloroprednisone, clobetasol, clobetasone, clocortolone, cloprednol, corticosterone, cortisone, cortivazol, deflazacort, desonide, desoximetasone, dexamethasone, diflorasone, diflucortolone, difluprednate, enoxolone, fluazacort, flucloronide, flumehtasone, flunisolide, fluocinolone acetonide, fluocinonide, fluocortin butyl, fluocortolone, fluorometholone, fluperolone acetate, fluprednidene acetate, fluprednisolone, flurandrenolide, fluticasone propionate, formocortal, halcinonide, halobetasol priopionate, halometasone, halopredone acetate, hydrocortamate, hydrocortisone, loteprednol etabonate, mazipredone, medrysone, meprednisone, methylprednisolone, mometasone furoate, paramethasone, prednicarbate, prednisolone, prednisolone 25-diethylaminoacetate, prednisone sodium phosphate, prednisone, prednival, prednylidene, rimexolone, tixocortal, triamcinolone, triamcinolone acetonide, triamcinolone benetonide, triamcinolone hexacetonide, and pharmaceutically acceptable salts thereof.

Exemplary non-steroidal anti-inflammatory therapeutic agents include, but are not limited to, aminoarylcarboxylic acid derivatives such as enfenamic acid, etofenamate, flufenamic acid, isonixin, meclofenamic acid, mefanamic acid, niflumic acid, talniflumate, terofenamate and tolfenamic acid; arylacetic acid derivatives such as acemetacin, alclofenac, amfenac, bufexamac, cinmetacin, clopirac, diclofenac sodium, etodolac, felbinac, fenclofenac, fenclorac, fenclozic acid, fentiazac, glucametacin, ibufenac, indomethacin, isofezolac, isoxepac, lonazolac, metiazinic acid, oxametacine, proglumetacin, sulindac, tiaramide, tolmetin and zomepirac; arylbutyric acid derivatives such as bumadizon, butibufen, fenbufen and xenbucin; arylcarboxylic acids such as clidanac, ketorolac and tinoridine; arylpropionic acid derivatives such as alminoprofen, benoxaprofen, bucloxic acid; carprofen, fenoprofen, flunoxaprofen, flurbiprofen, ibuprofen, ibuproxam, indoprofen, ketoprofen, loxoprofen, miroprofen, naproxen, oxaprozin, piketoprofen, pirprofen, pranoprofen, protizinic acid, suprofen and tiaprofenic acid; pyrazoles such as difenamizole and epirizole; pyrazolones such as apazone, benzpiperylon, feprazone, mofebutazone, morazone, oxyphenbutazone, phenybutazone, pipebuzone, propyphenazone, ramifenazone, suxibuzone and thiazolinobutazone; salicylic acid derivatives such as acetaminosalol, aspirin, benorylate, bromosaligenin, calcium acetylsalicylate, diflunisal, etersalate, fendosal, gentisic acid, glycol salicylate, imidazole salicylate, lysine acetylsalicylate, mesalamine, morpholine salicylate, 1-naphthyl salicylate, olsalazine, parsalmide, phenyl acetylsalicylate, phenyl salicylate, salacetamide, salicylamine o-acetic acid, salicylsulfuric acid, salsalate and sulfasalazine; thiazinecarboxamides such as droxicam, isoxicam, piroxicam and tenoxicam; others such as ε-acetamidocaproic acid, s-adenosylmethionine, 3-amino-4-hydroxybutyric acid, amixetrine, bendazac, benzydamine, bucolome, difenpiramide, ditazol, emorfazone, guaiazulene, nabumetone, nimesulide, orgotein, oxaceprol, paranyline, perisoxal, pifoxime, proquazone, proxazole and tenidap; and pharmaceutically acceptable salts thereof.

Exemplary narcotic analgesic therapeutic agents include, but are not limited to, alfentanil, allylprodine, alphaprodine, anileridine, benzylmorphine, bezitramide, buprenorphine, butorphanol, clonitazene, codeine, codeine methyl bromide, codeine phosphate, codeine sulfate, desomorphine, dextromoramide, dezocine, diampromide, dihydrocodeine, dihydrocodeinone enol acetate, dihydromorphine, dimenoxadol, dimepheptanol, dimethylthiambutene, dioxaphetyl butyrate, dipipanone, eptazocine, ethoheptazine, ethylmethylthiambutene, ethylmorphine, etonitazene, fentanyl, hydrocodone, hydromorphone, hydroxypethidine, isomethadone, ketobemidone, levorphanol, lofentanil, meperidine, meptazinol, metazocine, methadone hydrochloride, metopon, morphine, myrophine, nalbuphine, narceine, nicomorphine, norlevorphanol, normethadone, normorphine, norpipanone, opium, oxycodone, oxymorphone, papaveretum, pentazocine, phenadoxone, phenazocine, pheoperidine, piminodine, piritramide, proheptazine, promedol, properidine, propiram, propoxyphene, rumifentanil, sufentanil, tilidine, and pharmaceutically acceptable salts thereof.

Exemplary non-narcotic analgesic agents that may be combined with the sling 100 include, but are not limited to, aceclofenac, acetaminophen, acetaminosalol, acetanilide, acetylsalicylsalicylic acid, alclofenac, alminoprofen, aloxiprin, aluminum bis(acetylsalicylate), aminochlorthenoxazin, 2-amino-4-picoline, aminopropylon, aminopyrine, ammonium salicylate, amtolmetin guacil, antipyrine, antipyrine salicylate, antrafenine, apazone, aspirin, benorylate, benoxaprofen, benzpiperylon, benzydamine, bermoprofen, brofenac, p-bromoacetanilide, 5-bromosalicylic acid acetate, bucetin, bufexamac, bumadizon, butacetin, calcium acetylsalicylate, carbamazepine, carbiphene, carsalam, chloralantipyrine, chlorthenoxazin(e), choline salicylate, cinchophen, ciramadol, clometacin, cropropamide, crotethamide, dexoxadrol, difenamizole, diflunisal, dihydroxyaluminum acetylsalicylate, dipyrocetyl, dipyrone, emorfazone, enfenamic acid, epirizole, etersalate, ethenzamide, ethoxazene, etodolac, felbinac, fenoprofen, floctafenine, flufenamic acid, fluoresone, flupirtine, fluproquazone, flurbiprofen, fosfosal, gentisic acid, glafenine, ibufenac, imidazole salicylate, indomethacin, indoprofen, isofezolac, isoladol, isonixin, ketoprofen, ketorolac, p-lactophenetide, lefetamine, loxoprofen, lysine acetylsalicylate, magnesium acetylsalicylate, methotrimeprazine, metofoline, miroprofen, morazone, morpholine salicylate, naproxen, nefopam, nifenazone, 5' nitro-2'propoxyacetanilide, parsalmide, perisoxal, phenacetin, phenazopyridine hydrochloride, phenocoll, phenopyrazone, phenyl acetylsalicylate, phenyl salicylate, phenyramidol, pipebuzone, piperylone, prodilidine, propacetamol, propyphenazone, proxazole, quinine salicylate, ramifenazone, rimazolium metilsulfate, salacetamide, salicin, salicylamide, salicylamide o-acetic acid, salicylsulfuric acid, salsalte, salverine, simetride, sodium salicylate, sulfamipyrine, suprofen, talniflumate, tenoxicam, terofenamate, tetradrine, tinoridine, tolfenamic acid, tolpronine, tramadol, viminol, xenbucin, zomepirac, and pharmaceutically acceptable salts thereof.

Exemplary local anesthetic therapeutic agents include, but are not limited to, ambucaine, amolanone, amylocaine hydrochloride, benoxinate, benzocaine, betoxycaine, biphenamine, bupivacaine, butacaine, butaben, butanilicaine, butethamine, butoxycaine, carticaine, chloroprocaine hydrochloride, cocaethylene, cocaine, cyclomethycaine, dibucaine hydrochloride, dimethisoquin, dimethocaine, diperadon hydrochloride, dyclonine, ecgonidine, ecgonine, ethyl chloride, beta-eucaine, euprocin, fenalcomine, fomocaine, hexylcaine hydrochloride, hydroxytetracaine, isobutyl p-aminobenzoate, leucinocaine mesylate, levoxadrol, lidocaine, mepivacaine, meprylcaine, metabutoxycaine, methyl chloride, myrtecaine, naepaine, octacaine, orthocaine, oxethazaine, parethoxycaine, phenacaine hydrochloride, phenol, piperocaine, piridocaine, polidocanol, pramoxine, prilocaine, procaine, propanocaine, proparacaine, propipocaine, propoxycaine hydrochloride, pseudococaine, pyrrocaine, ropavacaine, salicyl alcohol, tetracaine hydrochloride, tolycaine, trimecaine, zolamine, and pharmaceutically acceptable salts thereof.

Exemplary antispasmodic therapeutic agents include, but are not limited to, alibendol, ambucetamide, aminopromazine, apoatropine, bevonium methyl sulfate, bietamiverine, butaverine, butropium bromide, n-butylscopolammonium bromide, caroverine, cimetropium bromide, cinnamedrine, clebopride, coniine hydrobromide, coniine hydrochloride, cyclonium iodide, difemerine, diisopromine, dioxaphetyl butyrate, diponium bromide, drofenine, emepronium bromide, ethaverine, feclemine, fenalamide, fenoverine, fenpiprane, fenpiverinium bromide, fentonium bromide, flavoxate, flopropione, gluconic acid, guaiactamine, hydramitrazine, hymecromone, leiopyrrole, mebeverine, moxaverine, nafiverine, octamylamine, octaverine, oxybutynin chloride, pentapiperide, phenamacide hydrochloride, phloroglucinol, pinaverium bromide, piperilate, pipoxolan hydrochloride, pramiverin, prifinium bromide, properidine, propivane, propyromazine, prozapine, racefemine, rociverine, spasmolytol, stilonium iodide, sultroponium, tiemonium iodide, tiquizium bromide, tiropramide, trepibutone, tricromyl, trifolium, trimebutine, n-trimethyl-3,3-diphenyl-propylamine, tropenzile, trospium chloride, xenytropium bromide, and pharmaceutically acceptable salts thereof.

The agent may be associated with the device 100 in a variety of manners. For example, the agent may be chemically or physically attached to the surface of the device 100. In one illustrative embodiment, the surface of the device 100 and the agent, for example, in solution, have complementary ionic charges. As such, when placed on the device 100, the agent ionically bonds to its surface. In another illustrative embodiment, before application of the agent, the protective treatment is applied to the device 100. According to another illustrative embodiment, the protective treatment and the agent are mixed to form a single treatment and then applied to the device 100 in a one step process. According to the invention, any suitable process may be employed for associating the agent with the device 100, such that the agent can leach to tissue in the region of the implanted device 100 and/or the protective treatment can dissolve and/or leach into the tissue in the region of the implanted device 100.

Figure 2:
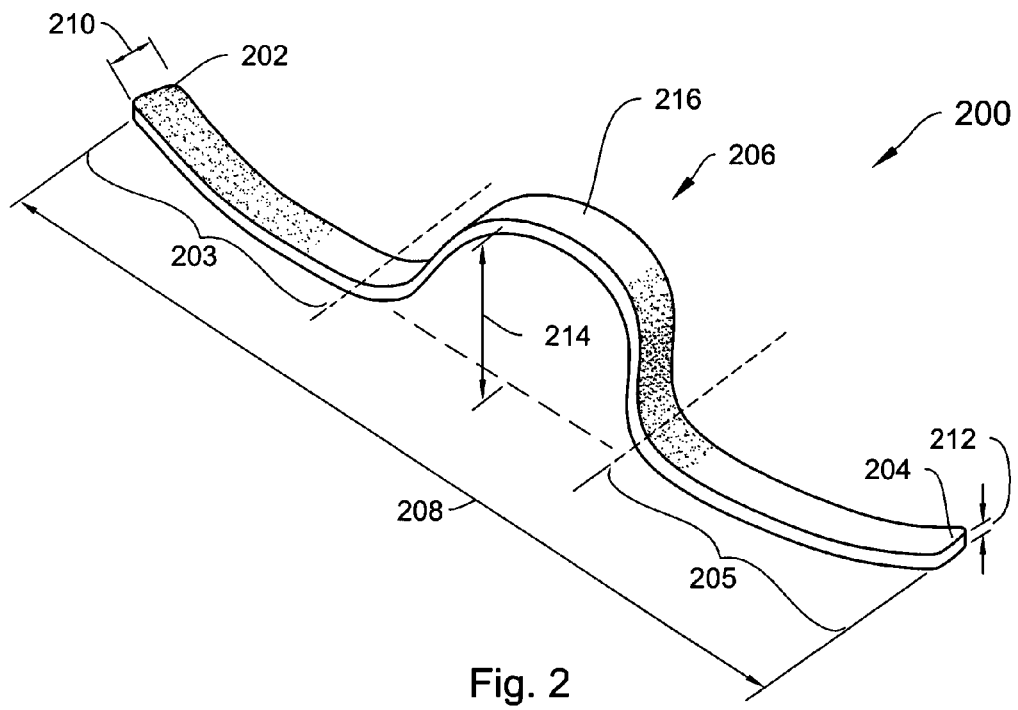
FIG. 2 is a top perspective view of a sling-like supportive device formed from a shape-resilient material and having an intermediate portion that is curved upward to a greater degree than the embodiment of FIG. 1 according to another illustrative embodiment of the invention.

FIG. 2 shows a top perspective view of a sling-like supportive device 200, similar to the illustrative embodiment of FIG. 1, formed from a shape-resilient material and having an intermediate portion that is curved upward for supporting an anatomical location according to another illustrative embodiment of the invention.

As in the case of the device 100, the device 200 includes first 202 and second 204 ends and an intermediate portion 206 located between the first 202 and second 204 ends. The device also includes a first axially peripheral section 203 extending between the first end 202 and the intermediate portion 206, and a second axially peripheral section 205 extending between the intermediate portion 206 and the second end 204. The illustrative device 200 is sized and shaped in a similar fashion to the device 100. In a similar fashion to the device 100, the device 200 includes a mid location 216, which is preferably located under the anatomical site to be supported. As also in the case of the device 100, the intermediate portion 206 is curved upward by a height 214 relative to a plane of the peripheral sections 203 and 205. One difference between the configurations of FIGS. 1 and 2 is that the height 214 may be greater than about 5 cm. Another difference is that the ends 202 and 204 do not turn upwards as sharply relative to the peripheral sections 203 and 205, respectively, as the ends 102 and 104 do relative to the peripheral sections 103 and 105, respectively. Instead, the peripheral sections 203 and 205 curve upwards gradually toward the device ends 202 and 204, respectively. The length 208, width 210 and thickness 212 of the device 200 are similarly dimensioned to the device 100. All of the other features discussed above with regard to the device 100 are equally applicable to the device 200.

Figure 3:
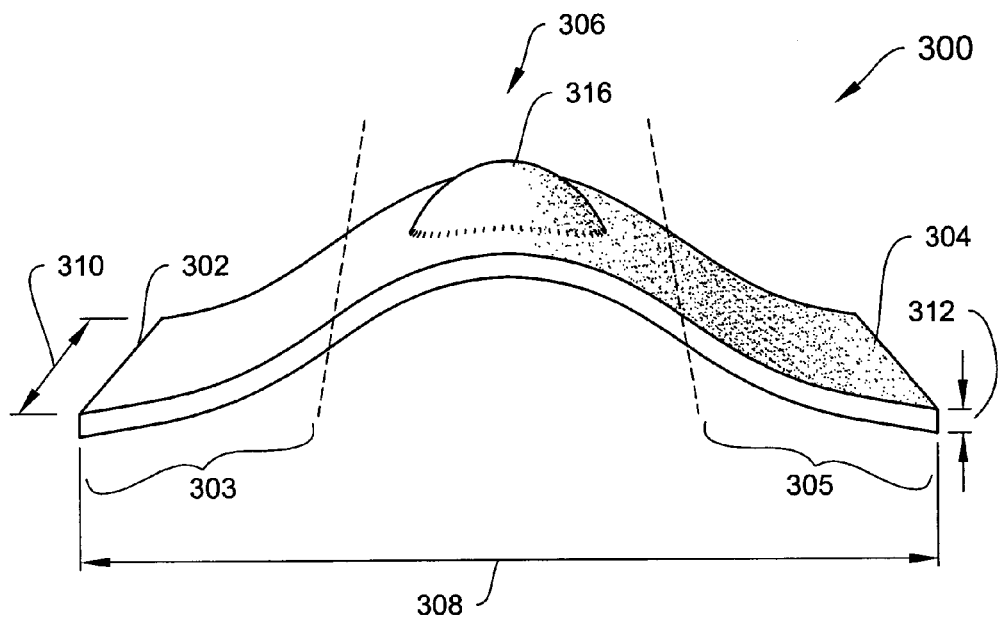
FIG. 3 is a top perspective view of a sling-like supportive device formed from a shape-resilient material and including a raised feature along an upwardly curved intermediate portion for supporting an anatomical location according to another illustrative embodiment of the invention.

FIG. 3 shows a top perspective view of a sling-like supportive device 300 including a raised feature along an upwardly curved intermediate portion for supporting an anatomical location according to another illustrative embodiment of the invention. The illustrative device 300 is sized and shaped in a similar fashion to the devices 100 and 200, and made with shape-resilient material. As in the case of the devices 100 and 200, the device 300 includes first 302 and second 304 ends and an intermediate portion 306 located between the first 302 and second 304 ends. Axially peripheral sections 303 and 305 extend between the intermediate portion 306 and the first 302 and second 304 ends, respectively. The device 300 is intended to be used in a manner similar to the devices 100 and 200. However, one difference in the configuration of the device 300 is that it includes a mid location 316 which is elevated in relation to the rest of the intermediate portion 306, not extending across the entire width of the device 300. In alternative embodiments the mid location 316 may extend across the entire width of the device 300. Additionally, while the mid location 316 is depicted being dome shaped in FIG. 3, in alternative configurations, it may have any suitable shape, including having a relatively flat top. The mid location 316 of the intermediate portion 306 may be textured so that the anatomical location such as a urethra, which it supports when placed in a patient's body, tends not to slip off it. The axially peripheral sections 303 and 305 may be curved or straight, and in some embodiments substantially coplanar with each other in a similar configuration to the device 100, while in alternative embodiments at an angle to each other as each section 303 and 305 slope downward relative to the central portion 306. The ends 302 and 304 may turn upwards, downwards or extend straight relative to the peripheral sections 303 and 305. When placed in a patient's body, the device 300 is compressed in a manner similar to the devices 100 and 200 as described above. All of the features discussed above with regard to the devices 100 and 200, including the length 308, width 310 and thickness 312 dimensions, are equally applicable to the device 300.

Figure 4:
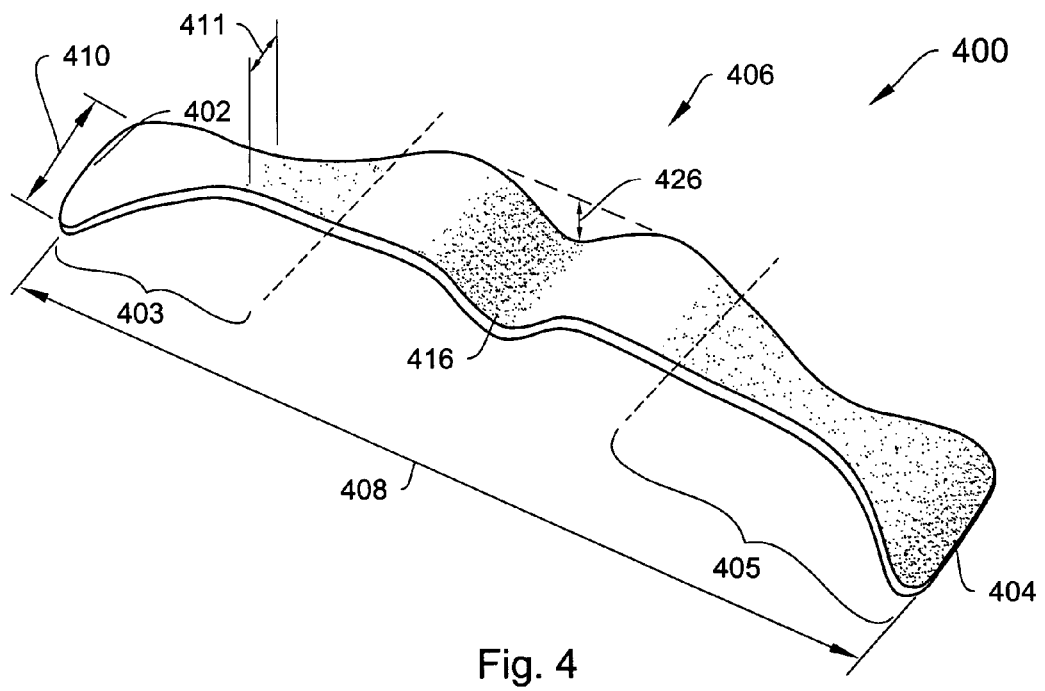
FIG. 4 is a top perspective view of a sling-like supportive device formed from a shape-resilient material and having end portions that are tapered laterally outward and a depression located along an intermediate portion for supporting an anatomical location according to another illustrative embodiment of the invention.

FIG. 4 shows a top perspective view of a sling-like supportive device 400 having end portions that are tapered laterally outward and a depression located along an intermediate portion for supporting an anatomical location according to another illustrative embodiment of the invention. The illustrative device 400 has an overall size similar to the devices 100, 200, and 300 and made from a shape-resilient material. As in the case of the device 100, the device 400 includes first 402 and second 404 ends and an intermediate portion 406 located between the first 402 and second 404 ends. The device also includes an axially peripheral section 403 extending between the end 402 and the intermediate portion 406, and an axially peripheral section 405 extending between the intermediate portion 406 and the end 404. In some embodiments, as shown in FIG. 4, the peripheral sections 403 and 405 generally slope downward from the intermediate portion 406. The peripheral sections 403 and 405 may be planar, or curve upward or downward. In alternative embodiments, the peripheral sections 403 and 405 are coplanar, similarly to the peripheral sections 103 and 105 of the device 100.

One difference between the device 400 and devices 100, 200, and 300 is that it includes a centrally located laterally extending depression 416. During implantation, the depression 416 is aligned with the urethra or bladder neck to essentially cradle the urethra or bladder neck to inhibit it from sliding off the device 400. According to another difference, the device has a reduced width 411 along at least a part of the axially peripherial sections 403 and 405. The length 408 is similar to the length 108 of the device 100. As shown as a depth 426, the depression 416 extends downward about 0.1 cm to about 1 cm from the highest point of the intermediate portion 406. In some configurations, the depth 426 of the depression 416 extends downward about 0.2 cm to about 0.5 cm. According to the illustrative embodiment, the width 411 is narrower than the width 410 by up to about 50%. In some configurations, the width 410 of the ends 402 and 404 is substantially the same as the width across the depression 416. The ends 402 and 404 may bend slightly downward, upward or may be straight compared to the planes of the respective axially peripheral sections 403 and 405. Other features discussed above with regard to the devices 100, 200, and 300 are equally applicable to the device 400.

Figure 5:
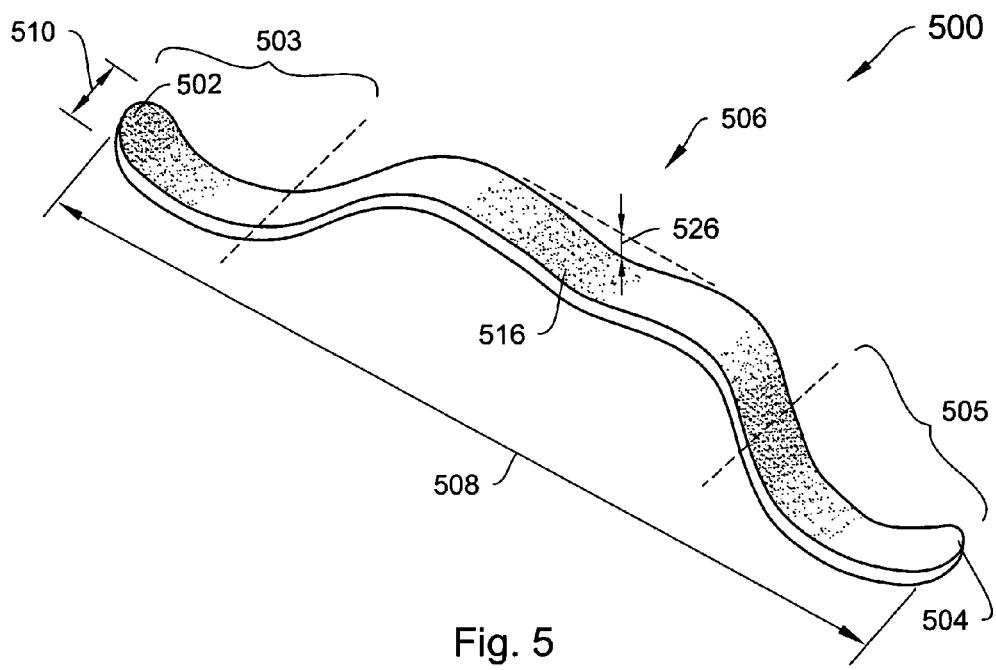
FIG. 5 is a top perspective view of a sling-like supportive device formed from a shape-resilient material and having ends that are curved upward, a raised intermediate portion, and a substantially centrally located depression for supporting an anatomical location according to another illustrative embodiment of the invention.

FIG. 5 shows a top perspective view of another illustrative embodiment of the invention, a sling-like supportive device 500 having ends that are curved upward, a raised intermediate portion, and a substantially centrally located laterally extending depression for supporting an anatomical location. As in the case of the device 400, the illustrative device 500 is formed from a shape-resilient material and configured similarly to the device 400 of FIG. 4. More particularly, the device 500 includes first 502 and second 504 ends and an intermediate portion 506 located between the ends 502 and 504. The device 500 also includes axially peripheral sections 503 and 505 located between the end 502 and the intermediate portion 506 and between the end 504 and the intermediate portion 506, respectively. The device 500 also includes a centrally located depression 516 in the intermediate portion 506. One difference between the device 500 and the device 400 is that the depth 526 of the depression 516 is less than the depth 426 of the depression 416. Another difference is that the device 500 has substantially the same width 510 throughout its axial length, more like devices 100 and 200. In some embodiments, the ends 502 and 504 curve upward in a similar fashion to the ends 102 and 104 of the device 100. In other embodiments, the ends 502 and 504 are configured similarly to the ends 202 and 204 of the device 200. The length 508 and the width 510 of the device 500 are similarly sized to the length 108 and width 110 of the device 100. Other features discussed above with regard to the devices 100, 200, 300, and 400 may be equally applicable to the device 500.

Figure 6:
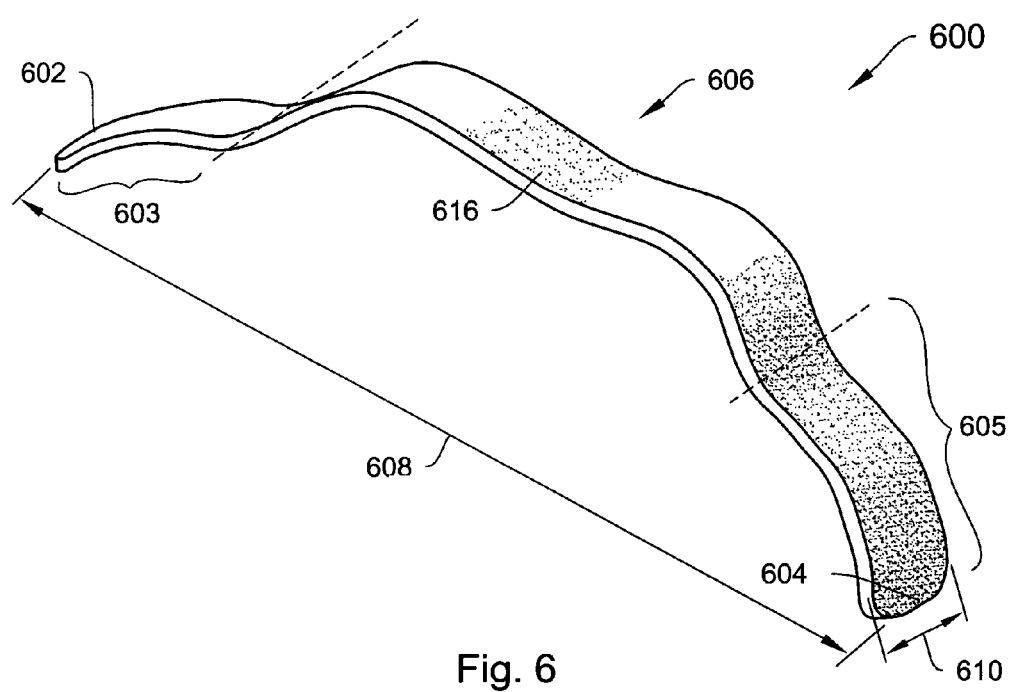
FIG. 6 is a top perspective view of a sling-like supportive device formed from a shape-resilient material and having ends that are curved downward, a raised intermediate portion, and a substantially centrally located depression for supporting an anatomical location according to another illustrative embodiment of the invention.

FIG. 6 shows a top perspective view of a sling-like supportive device 600 formed from a shape-resilient material having ends that are curved downward, a raised intermediate portion, and a substantially centrally located depression for supporting an anatomical location according to another illustrative embodiment of the invention. As shown, the device 600 is configured similarly to the devices 400 and 500 in that it includes a centrally located depression 616. It also includes ends 602 and 604, an intermediate section 606, and axially peripheral sections 603 and 605, extending between the intermediate section 606 and the ends 602 and 604, respectively. One difference between the device 500 and the device 600 is that the ends 602 and 604 turn downward like the ends 402 and 404 of the device 400, rather than upward like the ends 502 and 504 of the device 500. According to another difference, in some embodiments, the width 610 at each end 602 and 604 tapers gradually smaller from the ends 602 and 604 to the centrally located depression 616. According to the illustrative embodiment, the width 610 ranges from about 1 cm to about 2 cm at the ends 602 and 604, and gradually narrows toward the depression 616, by about 10% to about 50%. In some embodiments, the width 610 is substantially constant along the length 608 of the intermediate section 606. In another embodiment, the width 610 further narrows within the intermediate section 606, attaining the smallest width at the mid point of the centrally located depression 616. The length 608 is comparable to the lengths 108, 208, 308, 408 and 508 of the previously described embodiments. Other features of the above discussed illustrative embodiments may be equally applicable to the device 600.

Figure 7:
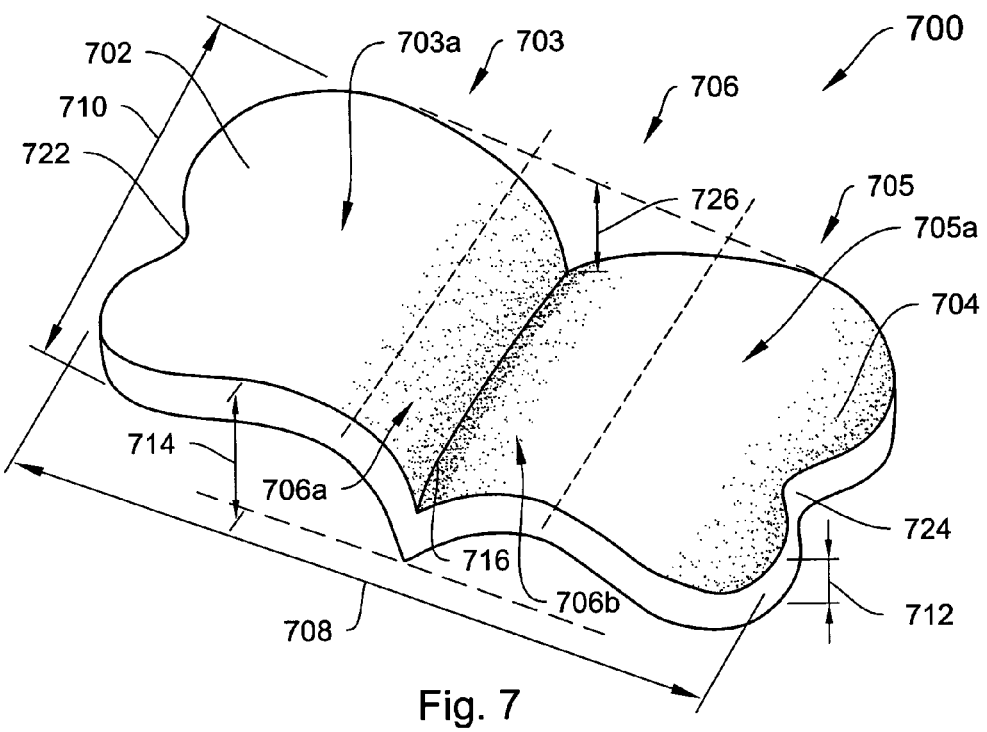
FIG. 7 is a top perspective view of a sling-like supportive device formed from a shape-resilient material and having a butterfly-like shape with a substantially centrally located laterally extending depression for supporting an anatomical location according to illustrative embodiment of the invention.

FIG. 7 shows a top perspective view of a sling-like supportive device 700 having a butterfly-like shape with a substantially centrally located laterally extending depression for supporting an anatomical location according to another illustrative embodiment of the invention. As with other illustrative devices described herein, the illustrative device 700 is formed from a shape-resilient material. The device 700 has an overall "butterfly-like" or "open-book-like" configuration. The device 700 includes a first end 702 and a second end 704, and an intermediate portion 706 located between the ends 702 and 704. The device 700 also includes an axially peripheral section 703 located between the intermediate portion 706 and the end 702, and an axially peripheral section 705 located between the intermediate portion 706 and the end 704. The top surfaces 703a and 705a of the peripheral sections 703 and 705 respectively are convex. The intermediate portion 706 includes two curved surfaces 706a and 706b which are extensions of the top surfaces 703a and 705a respectively. The surfaces 706a and 706b meet to form a centrally located laterally extending depression 716. The depression 716 functions in a similar fashion to the depressions 416, 516, and 616 and may have depth 726 comparable to the depression depths 426 and 526, and which may extend down to or through a common plane shared by at least a part of the axially peripheral sections 703 and 705. More particularly, when implanted, the depression 716 is aligned with an anatomical location, such as a urethra or a bladder neck, to be supported by the device 700 and inhibits it from slipping off the device 700. A depth 726 of the depression 716 is similar to the depth 426 of the depression 416 of the device 400, and is about 0.1 cm to about 1 cm from the highest point of the device 700. In an illustrative embodiment, the device 700 includes a notch 722 at the end 702 and a second notch 724 at the end 704, which facilitate handling the device 700, for example by inhibiting it from slipping out of the fingers of a medical operator holding it. As in the case of the previously described devices, the device 700 is dimensioned for implantation into the periurethral tissues of a patient to provide a urethral platform, and any dimensions suitable for that purpose may be used. According to one illustrative configuration, the device 700 has a length 708 of about 2 cm to about 5 cm, and a width 710 of about 1 cm to about 2 cm. The illustrative device 700 has a thickness 712 of about 0.5 mm to about 3 mm, and a height 714 of about 0.2 cm to about 1.5 cm. Other features discussed above with regard to devices 100, 200, 300, 400, 500, and 600 may be equally applicable to the device 700.

Figure 8:
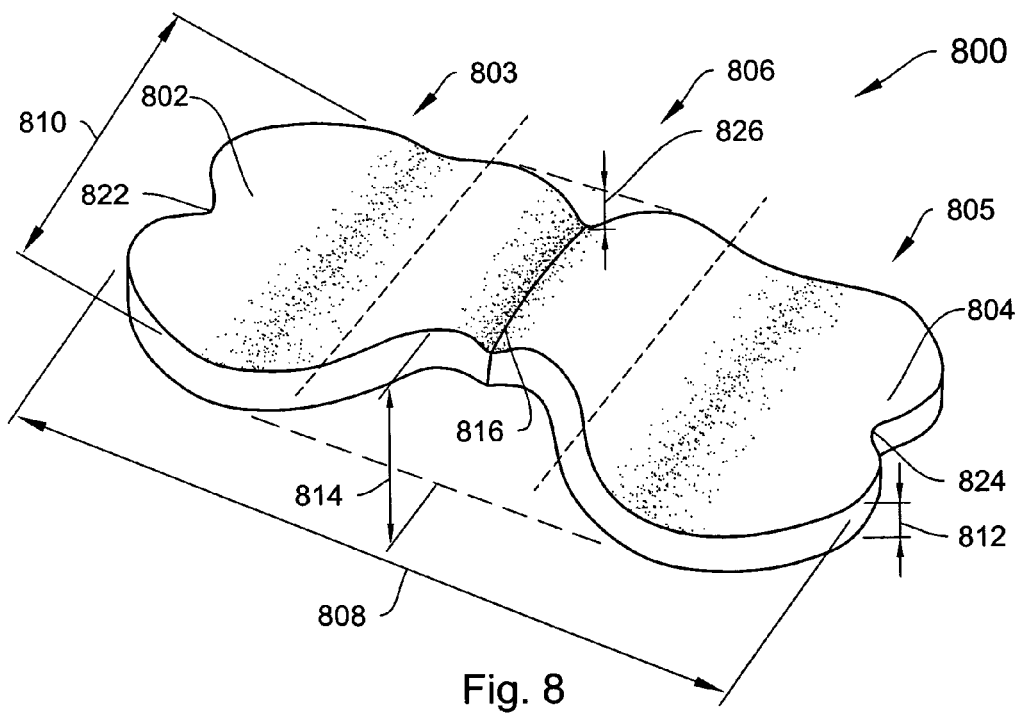
FIG. 8 is a top perspective view of a sling-like supportive device similar to the device of FIG. 7, but having a raised intermediate portion across which the lateral depression extends according to another illustrative embodiment of the invention.

FIG. 8 is a top perspective view of a sling-like supportive device similar to the device of FIG. 7, but having a raised intermediate portion across which the lateral depression extends according to another illustrative embodiment. The device 800 includes ends 802 and 804, an intermediate portion 806 located between the ends 802 and 804 and axially peripheral sections 803 and 805, located between the intermediate portion 806 and the ends 802 and 804, respectively. Like the device 700, the intermediate portion 806 includes a centrally located laterally extending depression 816, but unlike the device 700, and similar to the devices 400, 500 and 600, the intermediate portion 806 is raised relative to the peripheral sections 803 and 805 by a height 814 of about 0.2 cm to about 1.5 cm. The depression 816 functions in a similar fashion to the depressions 416, 516, 616. and 716, inhibiting slippage of an anatomical location off the device 800 when placed in a patient's body. The depression 816 has a depth 826, which is similar to the depth 426, and may extend up two or below a common plane shared by at least a part of the axially peripheral sections 803 and 805. The device 800 may include a notch 822 at the end 802 and a notch 824 at the end 804, similar to the notches 722 and 724 of the device 700 to function in a manner similar to the notches 722 and 724. A length 808, a width 810, and a thickness 812 of the device 800 are similar to the length 708, the width 710, and the thickness 814, respectively, of the device 700, and as in the case of the previously described devices, the device 800 may have any dimensions suitable for implantation into the periurethral tissues of a patient to provide a urethral platform. Other features discussed above with regard to devices 100, 200, 300, 400, 500, 600 and 700 may be equally applicable to the device 800.

Figure 9:
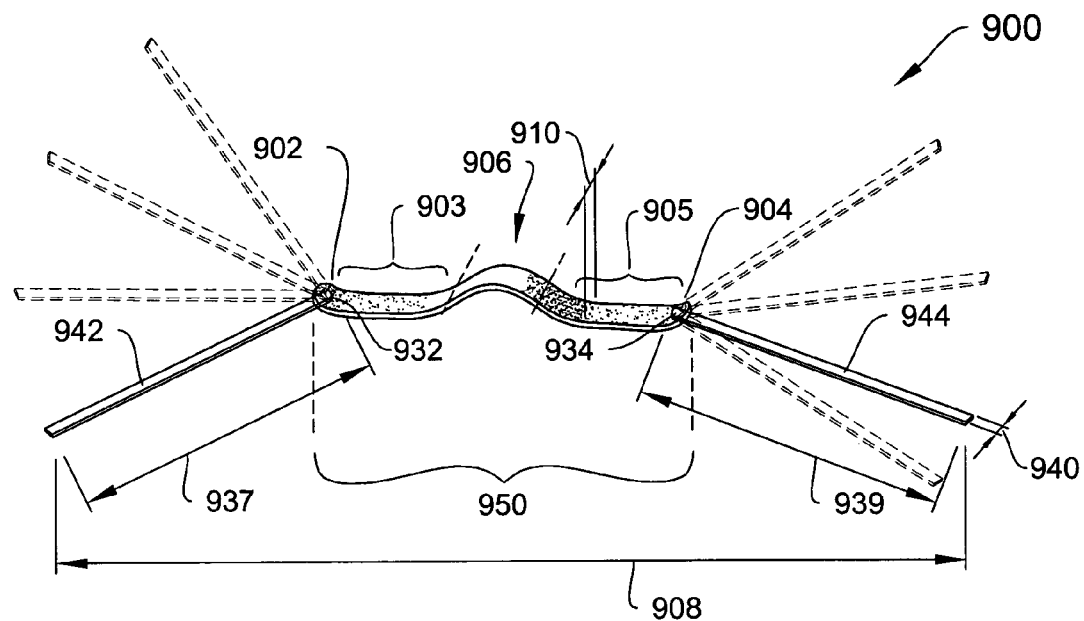
FIG. 9 is a top perspective view of a sling-like supportive device of the type depicted in FIG. 1 and including hinged extensions at each end for aiding in accurate placement of the device according to an illustrative embodiment of the invention.

FIG. 9 is a top perspective view of a sling-like supportive device 900, which is of the type depicted in FIG. 1 and including hinged extensions at each end for aiding in accurate placement of the device according to an illustrative embodiment. The illustrative device 900 is similar to the device 100, 200, 300, 400, 500, or 600 in overall size. The illustrative device 900 includes first 902 and second 904 ends and an intermediate portion 906 located between the ends 902 and 904. The device 900 also includes an axially peripheral section 903 extending between the end 902 and the intermediate portion 906, and a second axially peripheral section 905 extending between the intermediate portion 906 and the end 904. Similarly to the device 100, under rest conditions, the axially peripheral sections 103 and 105 are located substantially coplanar with each other, and the intermediate portion 106 curves upward out of the plane of the of the sections 103 and 105. The intermediate portion 906, the peripheral sections 103 and 105, and the ends 902 and 904 form a middle section 950 similar to the devices 100, 200, 300, 400, 500, and 600. A width 910 of the middle section 950 is similar to the widths 110, 210, 310, 410, 510, and 610, and in some embodiments may narrow similar to the width 411. The device 900 additionally includes a hinge point 932 near the end 902 and another hinge point 934 near the end 904, and an arm 942 extending from the hinge point 932 to extend a peripheral section 903 and a second arm 944 extending from the hinge point 934 to extend a peripheral section 905. The overall length 908 of the device 900 is similar to the length 108 described for the device 100. In illustrative embodiments, a first arm length 937 of the arm 942 and a second arm length 939 of the arm 944 are substantially equal and are each about 0.5 cm to about 4 cm. In some embodiments, the arms 942 and 944 have a width 940, which is substantially similar to the width 910 of the middle section 950. In other embodiments, the width 940 is narrower than the width 910, and is about 0.2 cm to about less than 2 cm. The hinge points 932 and 934 are designed to be movable by the hand of an operator or by a device such as a small wrench or a lever so that the arm 942 and the arm 944 extend upward, horizontally, or downward at various positions in relation to the peripheral sections 903 and 905, respectively, and in alternative embodiments, extend at various horizontal angles relative to the peripheral sections 903 and 905. The hinge points 932 and 934 are capable of locking in a position. By "locking in a position" it is meant that the arms 942 and 944 do not move to change angles in relation to the peripheral sections 903 and 905 respectively, from each position that was set by an operator, when placed in a patient's body at an anatomical location. In certain illustrative embodiments, the hinge points 932 and 934 are pivots, hinges, universal ball joints, or any suitable joints or joining mechanisms, such hinge points having notches for defined locking positions; having sufficient resistance to turning or moving against the force created, for example, from patient movement, muscle flexing, or anatomical size changes when the device 900 is placed in an anatomical location; or having any mechanism capable of locking in a position so that they remain locked in a position when the device 900 is placed in a patient's body in an anatomical location. All other features discussed above with regard to the device 100 are equally applicable to the device 900.

Figure 10A:
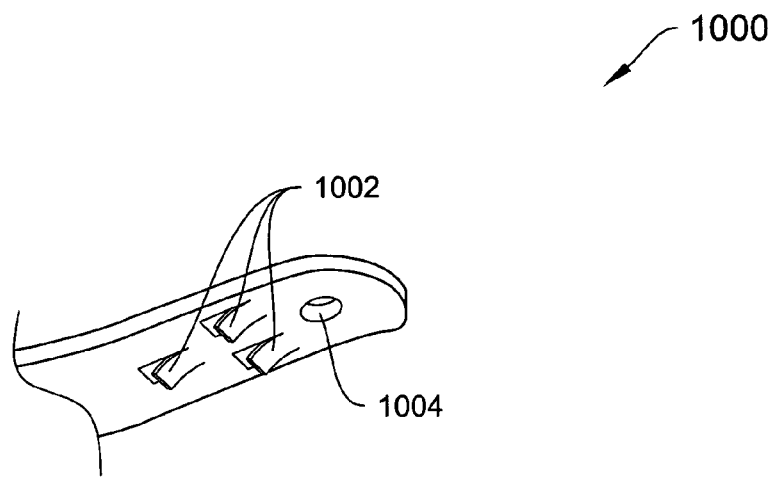
FIG. 10A is a bottom perspective view of an end of a sling-like supportive device of the type depicted in FIG. 1 and including laterally extending protrusions on a lower side near each end for engaging with the tissues of a patient to hold the device in place subsequent to placement according to an illustrative embodiment of the invention.
Figure 10B:
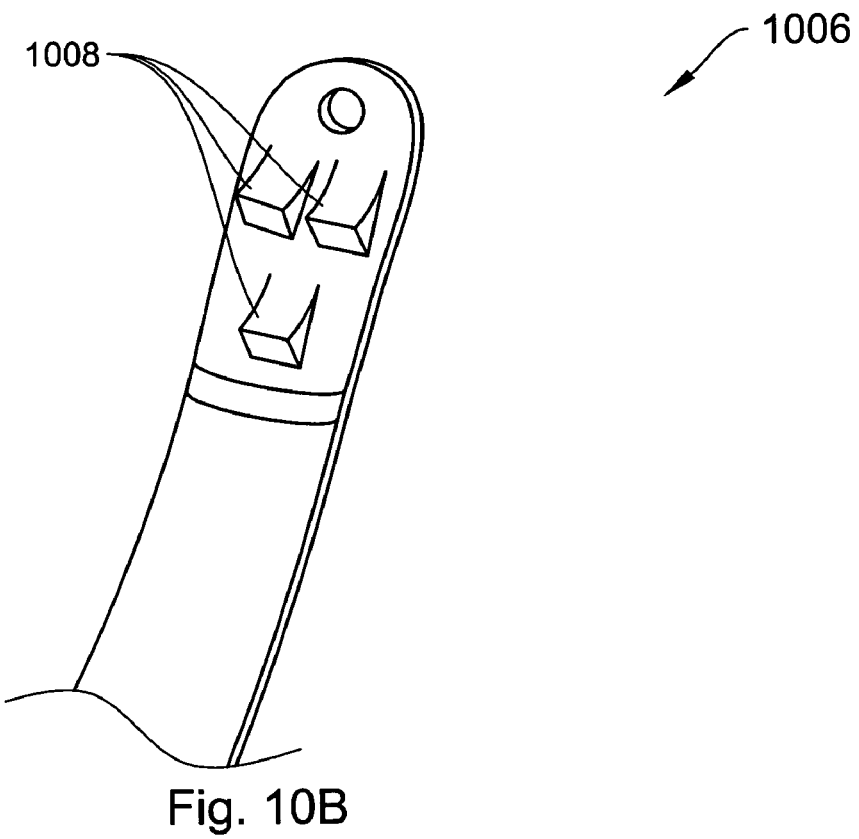
FIG. 10B is a bottom view showing an association element attached to an end of a sling-like supportive device of the type depicted in FIG. 1, the association element including laterally extending protrusions on a lower side for engaging with tissues of a patient and an axially extending inner channel according to another illustrative embodiment of the invention.
Figure 10C:
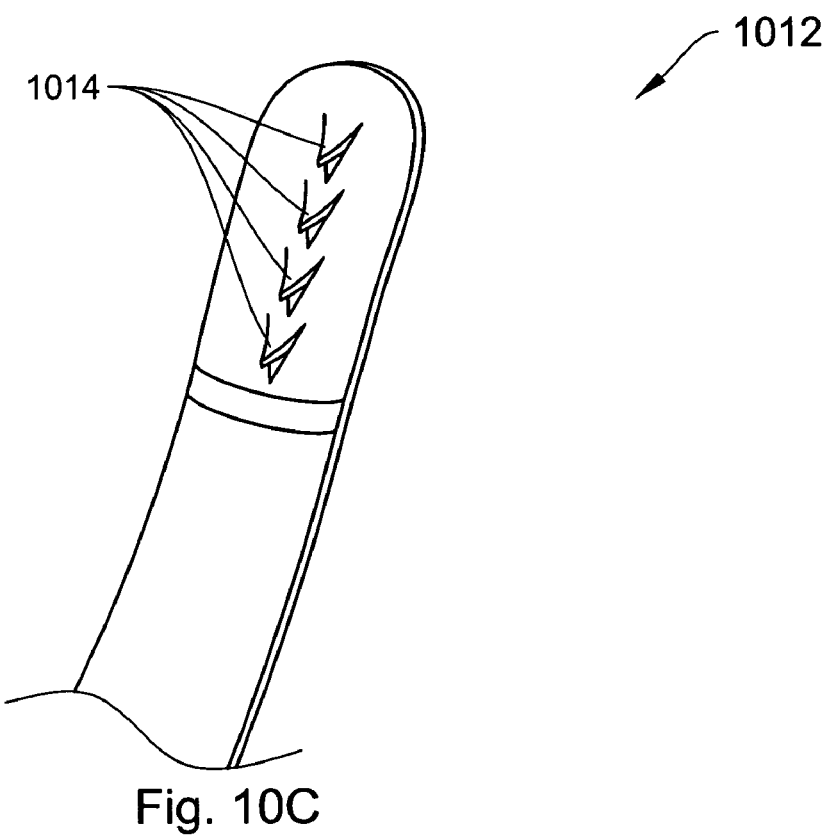
FIG. 10C is a bottom view of an association element attached to an end of a sling-like supportive device in a similar configuration to that depicted in FIG. 10B, but including differently configured laterally extending protrusions according to an illustrative embodiment of the invention.
Figure 12A:
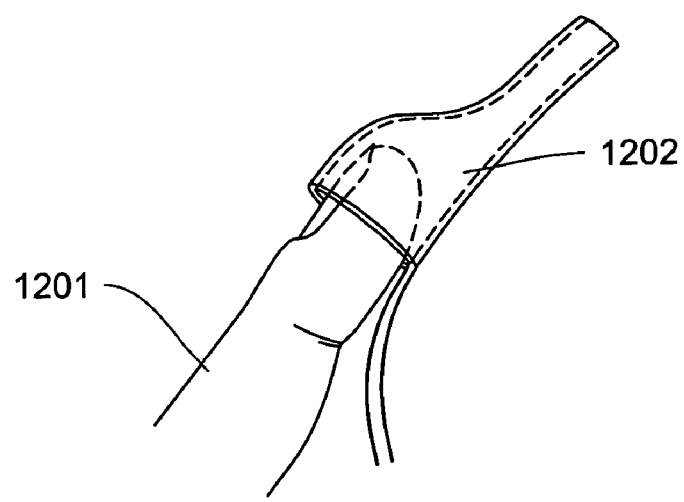
FIG. 12A is a perspective view showing an end of a sling-like supportive device of the type depicted in FIG. 1 and including an association element having an axially extending channel sized and shaped for interfitting over a finger of a medical operator to facilitate insertion of the device end into the periurethral tissues of a patient according to another illustrative embodiment of the invention.
Figure 12B:
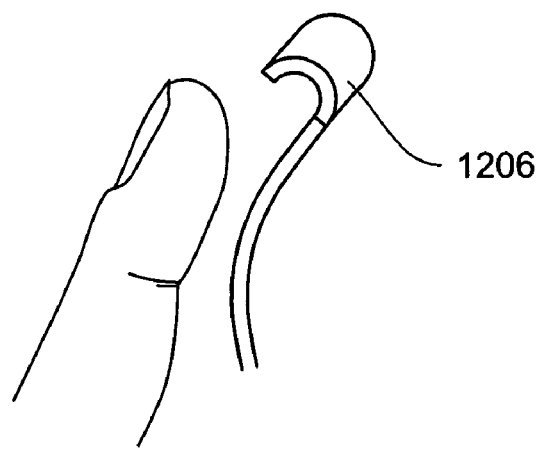
FIG. 12B is a side perspective view showing an end of a sling-like supportive device of the type depicted in FIG. 1 and including an association element sized and shaped for receiving a finger of a medical operator to facilitate insertion of the device end into the periurethral tissues of a patient according to another illustrative embodiment of the invention.
Figure 12C:
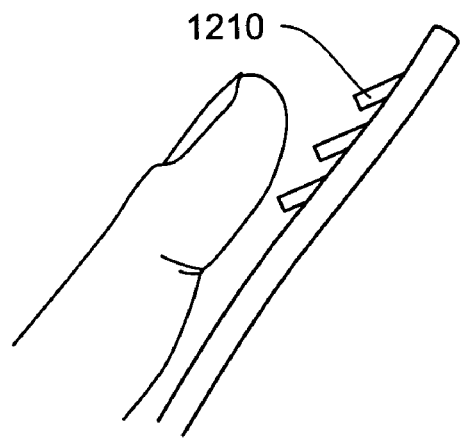
FIG. 12C is a side perspective view of a sling end of the type shown in 10A, wherein the laterally extending protrusions are further sized and shaped to engage with a finger of a medical operator to facilitate insertion of the device end into the periurethral tissues of a patient according to another illustrative embodiment of the invention.

FIG. 10A is a bottom perspective view of an end 100 of a sling-like supportive device of the invention, such as the illustrative devices 100, 200, 300, 400, 500, 600, and 900, including laterally extending projections 1002 on a lower side near each end of the device, for engaging with the tissues of a patient to hold the device in place subsequent to placement of the device in the patient. The end 1000 includes one or more laterally extending projections 1002 may have any shape suitable for affixing the anchor within an anatomical membrane, muscle, ligament, soft tissue, bone or other anatomical site. Projections 1002 may also be associated with some embodiments of the invention similar to devices 700 and 800. In some embodiments, the projections 1002 are angled downward to inhibit slippage of the device when the device is placed in the anatomical location. As described above, the projections 1002 may also promote tissue growth and beneficial scar tissue formation around a device including the projections 1002, aiding stabilizing the device and/or creating natural support for the anatomical location. The projections 1002 also aid a medical operator in placing a device of the invention in a correct anatomical location, by allowing the medical operator to push the device in a direction with a finger tip as illustrated in FIG. 12B or 12C. The projections 1002 can be on the top and/or bottom side of a device of the invention, and there can be one, two, three, or more protrusions 1002. In an illustrative embodiment, the projections 1002 are flexible, bending toward the body of the device when being inserted into an anatomical location, but projecting further out as the device rests in a location within a patient's body, or when force is exerted to remove the device from the anatomical location. In another illustrative embodiment, such as shown in FIG. 10B, the projections 1008 are solid and do not move relative to the body of the device. In other illustrative embodiments, such as shown in FIG. 10C, the projections 1014 may be rectangular, triangular, reverse triangular, curved, or any suitable shape for resisting removal of the device from the patient's body. Additionally, the projections 1002, 1008, and 1014 may be arranged in any pattern, such as one or more rows, or randomly. In some embodiments, projections described herein are made as part of a device and from the same material as the surface material of the device. In other embodiments, the projections are manufactured from biocompatible materials described above but different from the material that the device is manufactured from, and attached to the device in any suitable means, including using adhesives.

In some embodiments, the end 1000 of a device of the invention has a through aperture, such as the through aperture 1004 of FIG. 10A. The aperture 1004 has a diameter size of about 0.1 cm to about 0.5 cm and can be particularly sized for interfitting onto a distal end of the shaft of a delivery device, such as a delivery device 1300 shown in FIG. 13A, by placing a tip 1306 of the delivery device 1300 into the aperture 1004. In certain illustrative embodiments, the tip 1306 includes a slit 1310, separating the tip 1306 into two prongs 1307 and 1308. In certain embodiments, only one of the two prongs, either the prong 1307 or the prong 1308, fits into the aperture 1004, when the delivery device 1300 is in use. Any sling-like supportive device of the invention, including the illustrative device 700 or 800, may have part or all of one or both sides of the device to be textured and/or augmented with structural features similar to the projections 1002, 1008, and 1014, shown in FIGS. 10A, 10B and 10C. All features discussed above with regard to the device 100 are equally applicable to any device of the invention having features described here and exemplified in FIGS. 10A, 10B, and 10C.

Figure 11A:
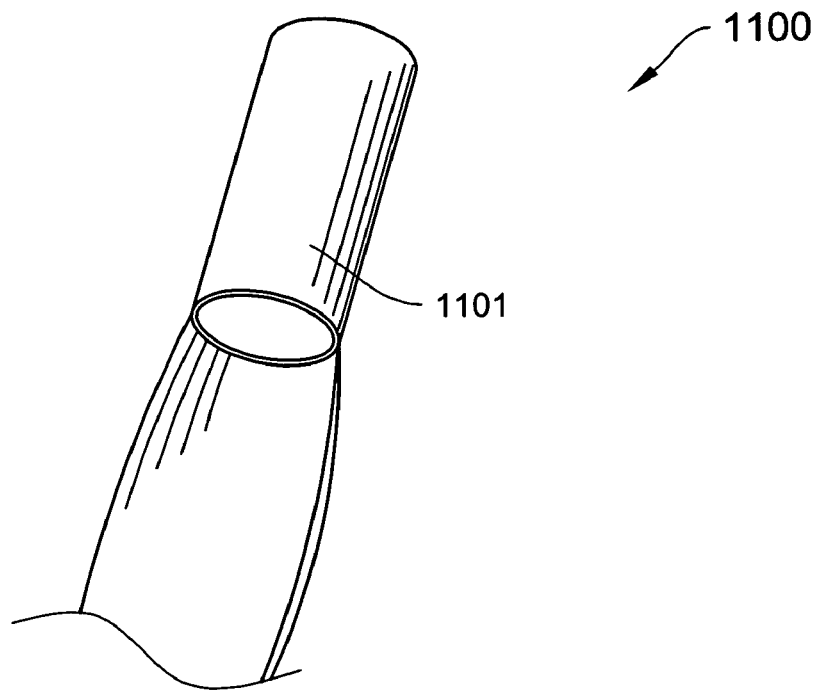
FIG. 11A is a bottom perspective view showing a dilator tube attached to an end of a sling-like supportive device of the type depicted in FIG. 1, the dilator tube being sized and shaped for slidably interfitting over a distal end of a delivery device shaft according to an illustrative embodiment of the invention.
Figure 11B:
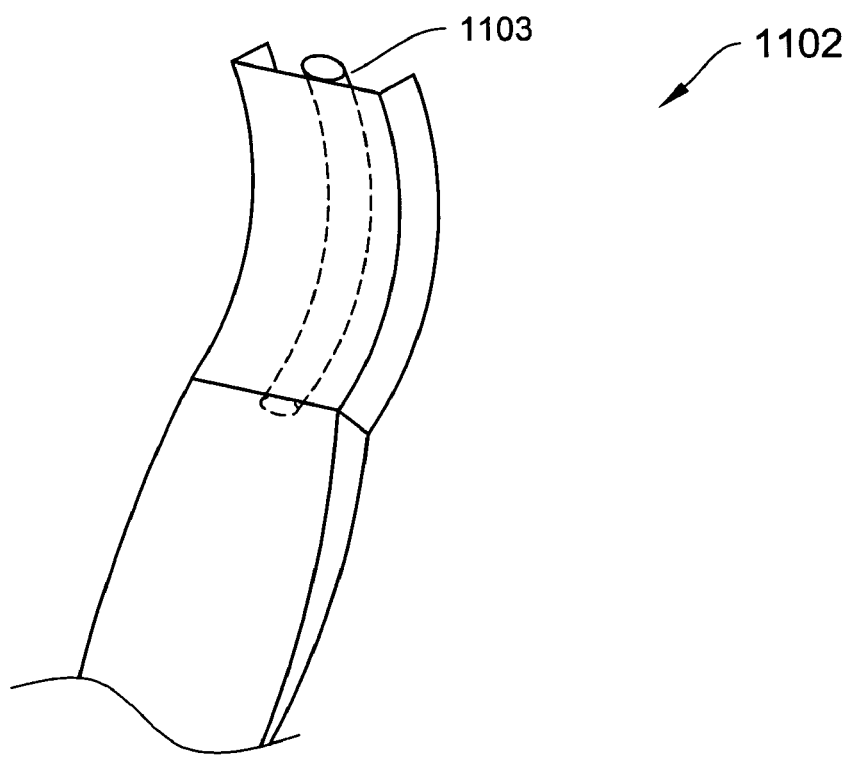
FIG. 11B is a bottom perspective view showing an end of a sling-like supportive device of the type depicted in FIG. 1 and including an association element located on each end sized and shaped for slidably engaging a delivery device according to another embodiment of the invention.
Figure 11C:
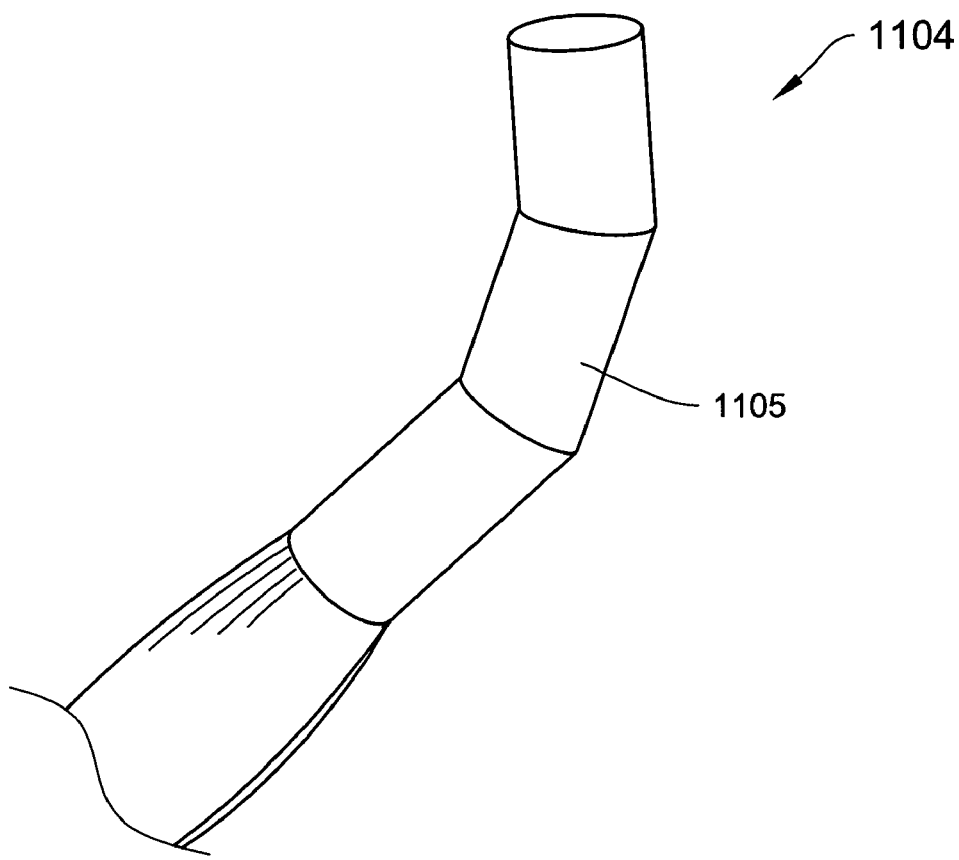
FIG. 11C is a perspective view showing a dilator tube attached to an end of a sling-like supportive device in a similar fashion to the embodiment of FIG. 11A, except with the dilator tube being longer and including multiple bends according to an alternative illustrative embodiment of the invention.
Figure 11D:
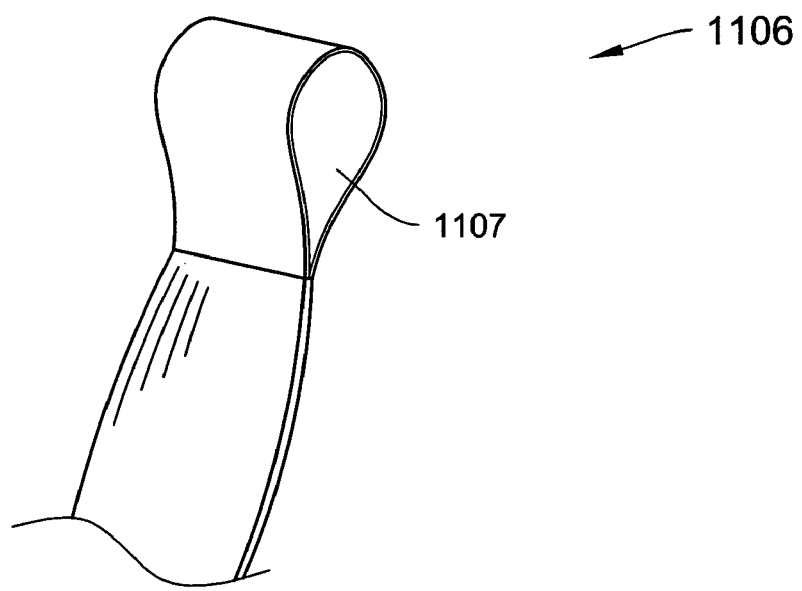
FIG. 11D is a perspective view showing an end of a sling-like supportive device of the type depicted in FIG. 1 and including a looped end portion for engaging with a delivery device for implantation in a patient according to an illustrative embodiment of the invention.

FIGS. 11A through 11D show perspective views of various illustrative forms of an end of a sling-like supportive device of the type depicted in FIGS. 1 through 9, or an end of a sleeve to be used in conjunction with a sling-like device, including a dilator tube or a loop connected to the device and sized and shaped for engaging with a delivery device for implantation of the sling-like device into a patient. FIG. 11A shows a short tube 1101 connected to an end 1100 of a device of the invention to engage with a delivery device. The tube 1101 is of uniform diameter and sized and shaped for interfitting with a delivery device such as the delivery device 1300. Alternatively, the tube 1101 narrows towards the distal end, and is sized and shaped for use with a medical operator's finger tip as a delivery device, as illustrated in FIG. 12A. FIG. 11B shows a tube 1103 attached to one side of an end 1102 of a device of the invention. FIG. 11C shows another tube 1105 with a segmented structure attached to an end 1104 of a device of the invention. Similarly to the tube 1101, tube 1103 and 1105 are sized and shaped for interfitting with a delivery device such as the delivery device 1300. FIG. 11D shows a loop 1107 connected at the end 1106 of a device of the invention and sized and shaped for hooking on the tip of a delivery device, such as the tip 1306 of the delivery device 1300. The tubes and loops described above, or any structure connected to the device to aid engaging a delivery device with the device, is made from biocompatible and/or biodegradable material described above. Features described herein and exemplified by FIGS. 11A to 11D may be found on any devices of the invention, and are applicable in addition to any of the features discussed above with regard to the device 100.

FIGS. 12A to 12C show a side view of a medical operator's finger engaged in an end of a device of the invention or a sleeve to be used with a device of the invention as the medical operator delivers the device into a patient's body. As shown in FIG. 12A and described above, a medical operator's finger 1201 fits into a tube 1202, a hook 1206, or projections 1210, allowing the medical operator to directionally push the end 1200 of a device into a patient's body.

Figures 13A, 13B:
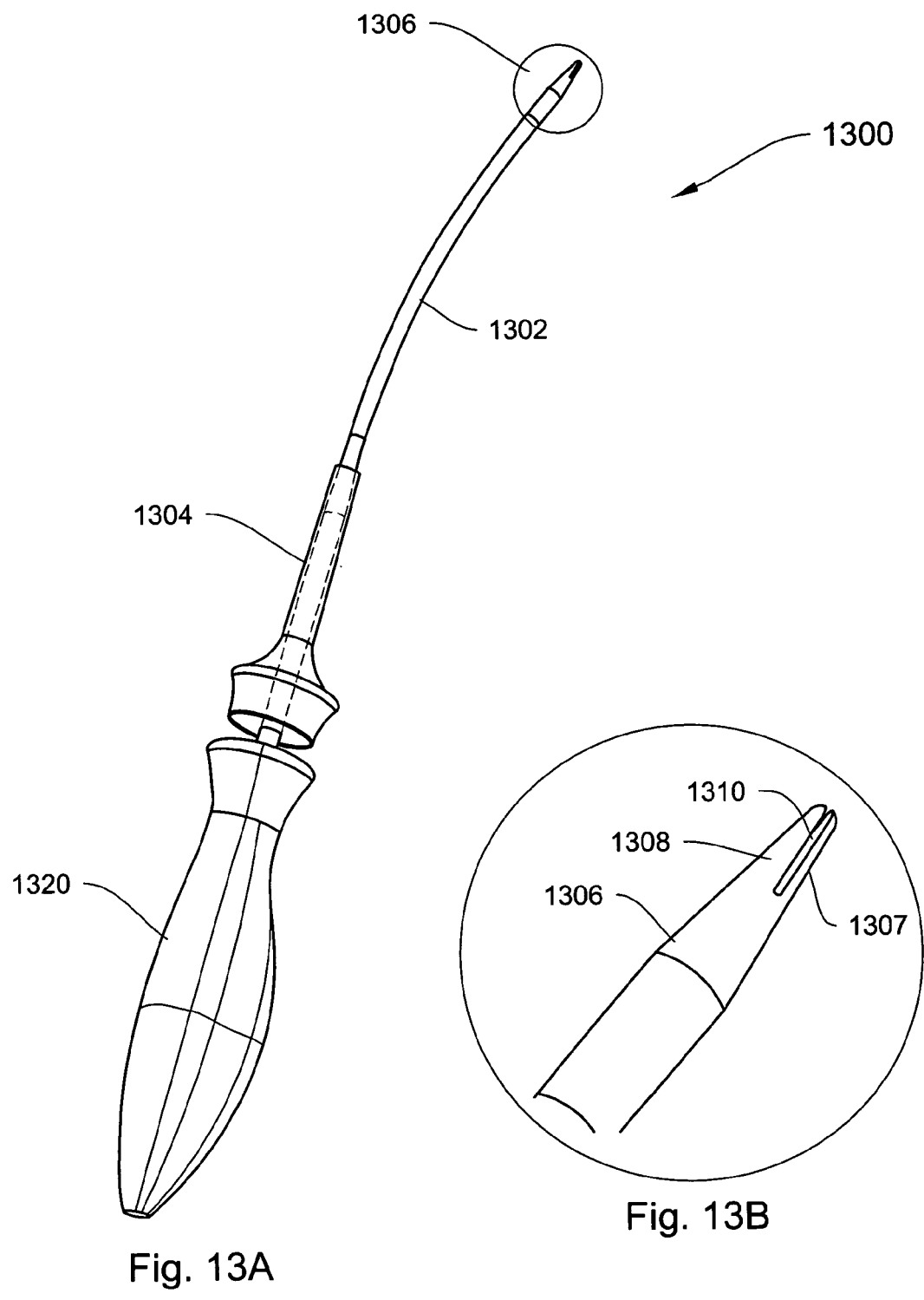
FIGS. 13A and 13B depict exemplary delivery devices for delivering the supportive device of the invention.

FIG. 13A shows a perspective view of an exemplary delivery device 1300, useful in delivering a device of the invention. The delivery device 1300 includes a handle 1320, a shaft 1302 which may be slightly curved, extending distally from a distal end of the handle 1320 and terminating at a distal end to form a conical tip 1306. The tip 1306 may have a slot 1310, which divides the tip 1306 into two parts 1308 and 1307. The shaft 1320 is permanently affixed to the handle 1320. The shaft 1302 of the delivery device 1300 is formed of surgical grade stainless steel and, excluding the conical tip 1306, has a constant diameter along its length. The delivery device 1300 also includes a pusher assembly 1304, which is slidably associated with the shaft 1302 and extends coaxially over a portion of the proximal end of the shaft 1302. When in use by a medical operator, the shaft 1302 may pass through a tube connected to a device of the invention, or to a sleeve that is associated with a device of the invention, such as the tubes 1101, 1103, and 1105, and the proximal end of a tube abuts against the distal end of the pusher assembly 1304. The medical operator then may slide the pusher assembly 1304 into the extended position to push the tube further into the body of the patient and disengage the tip 1306 of the delivery device 1300 from the interfitting part of the sling-like device, to remove the delivery device from the patient's body. According to other illustrative embodiments, the conical tip 1306 may interfit through an aperture in an end of the sling-like device of the invention, such as the aperture 1004. In further illustrative embodiments, the slot 1310 may engage with an end of the sling-like device.

A device of the invention may be used in conjunction with a sleeve that wholly or partially covers the device. The sleeve may have textures and/or projections as depicted in FIGS. 10A to 10C, or coated with one or more therapeutic agents, as described above. The sleeve may include a dilator tube or a loop, such as described above and depicted in FIGS. 11A to 11D, connected to the end of the sleeve and sized and shaped for engaging with a delivery device for implantation of the sling-like device into a patient. A sleeve that may be used in the assembly with the device of the present invention is described, for example, in WO02/071953A2, titled "System for implanting an implant and method thereof" incorporated in its entirety herein.

In another aspect, the invention is directed to methods for providing support to an anatomical location. In an illustrative example of this aspect of the invention, the anatomical location is the urethra, and the support the device provides is useful as treatment of urinary incontinence. An illustrative method of the invention, depicted in FIGS. 14A to 14C, includes the steps of surgically making an incision in proximity of an anatomical location in need of support, such as a urethra, and placing a sling-like device of the invention in the incision so that the tissue surrounding the incision provides force to compress or expand the device into a deformed shape different from a shape the device is in while outside the patient's body.

According to one procedure, the incision is substantially horizontal and long enough to enable a medical operator to place the sling-like device through the incision and into the patient's body, and made in or close to a location where a conventional sling or mesh for support of the anatomical location would sit. In one illustrative embodiment, the incision is made in the vaginal wall or other naturally existing body cavity or in between tissues. In another illustrative embodiment, the incision is long enough to accommodate the length of the device 100 to be placed in a patient's body. The device 100 is placed through the incision so that the length 108 is aligned with the length of the incision. The sling-like device 100 is positioned so that it is substantially horizontal, and the mid location 116 is under an anatomical location to be supported. In an example where the anatomical location is a urethra, the device 100 is positioned so that the length 108 is substantially perpendicular to the longitudinal direction of the urethra.

According to some methods, the ends of the supportive device are located in the obturator membrane.

Compression and/or extension of the inserted device generates the counterforce, and the device pushes back the tissues surrounding it, including the anatomical location in need of support. Because the device is inserted in the lower proximity of an anatomical location, for example a urethra, the compression and/or extension creates an upward force to support the anatomical location. The counterforce generated is larger when the tissue exerts larger compression or expansion force to the inserted device. Therefore, the device automatically provides larger supporting force when the patient tenses muscles, for example due to sneezing or laughing.

Without limitation, examples slings, sling assemblies, sling delivery devices and approaches, sling assembly-to-delivery device association mechanisms, and sling anchoring mechanisms including features than may be employed with the invention are disclosed in U.S. Pat. No. 6,042,534 entitled "Stabilization sling for use in minimally invasive pelvic surgery," U.S. Pat. No. 6,755,781 entitled "Medical slings," U.S. Pat. No. 6,666,817 entitled "Expandable surgical implants and methods of using them," U.S. Pat. No. 6,042,592 entitled "Thin soft tissue surgical support mesh," U.S. Pat. No. 6,375,662 entitled "Thin soft tissue surgical support mesh," U.S. Pat. No. 6,669,706 entitled "Thin soft tissue surgical support mesh," U.S. Pat. No. 6,752,814 entitled "Devices for minimally invasive pelvic surgery," U.S. patent application Ser. No. 10/918,123 entitled "Surgical Slings," U.S. patent application Ser. No. 10/641,376 entitled "Spacer for sling delivery system," U.S. patent application Ser. No. 10/641,192 entitled "Medical slings," U.S. Ser. No. 10/641,170 entitled "Medical slings," U.S. Ser. No. 10/640,838 entitled "Medical implant," U.S. patent application Ser. No. 10/460,112 entitled "Medical slings," U.S. patent application Ser. No. 10/631,364 entitled "Bioabsorbable casing for surgical sling assembly," U.S. Ser. No. 10/092,872 entitled "Medical slings," U.S. patent application Ser. No. 10/939,191 entitled "Devices for minimally invasive pelvic surgery," U.S. patent application Ser. No. 10/774,842 entitled "Devices for minimally invasive pelvic surgery," U.S. patent application Ser. No. 10/774,826 entitled "Devices for minimally invasive pelvic surgery," U.S. Ser. No. 10/015,114 entitled "Devices for minimally invasive pelvic surgery," U.S. patent application Ser. No. 10/973,010 entitled "Systems and methods for sling delivery and placement," U.S. patent application Ser. No. 10/957,926, entitled "Systems and methods for delivering a medical implant to an anatomical location in a patient," U.S. patent application Ser. No. 10/939,191 entitled "Devices for minimally invasive pelvic surgery," U.S. patent application Ser. No. 10/918,123 entitled "Surgical slings," U.S. patent application Ser. No. 10/832,653 entitled "Systems and methods for sling delivery and placement," U.S. patent application Ser. No. 10/642,397 entitled "Systems, methods and devices relating to delivery of medical implants," U.S. patent application Ser. No. 10/642,395 entitled "Systems, methods and devices relating to delivery of medical implants," U.S. patent application Ser. No. 10/642,365 entitled "Systems, methods and devices relating to delivery of medical implants," U.S. patent application Ser. No. 10/641,487 entitled "Systems, methods and devices relating to delivery of medical implants," U.S. patent application Ser. No. 10/094,352 entitled "System for implanting an implant and method thereof," U.S. patent application Ser. No. 10/093,498 entitled "System for implanting an implant and method thereof," U.S. patent application Ser. No. 10/093,450 entitled "System for implanting an implant and method thereof," U.S. patent application Ser. No. 10/093,424, entitled "System for implanting an implant and method thereof," U.S. patent application Ser. No. 10/093,398, entitled "System for implanting an implant and method thereof," and U.S. patent application Ser. No. 10/093,371 entitled "System for implanting an implant and method thereof," the entire contents of all of which are incorporated herein by reference.

Variations, modifications, and other implementations of what is described may be employed without departing from the spirit and the scope of the invention.

What is claimed is:

1. An implantable support comprising,
   a semi-rigid body comprising a substantially uniform thickness sized and shaped for providing a urethral platform for treating urinary incontinence, the body having an initial shape when under rest conditions and-being formed from a singular shape-resilient synthetic material that is non-destructively and reversibly deformable, said body having first and second axial peripheral sections with terminal ends and an intermediate portion between the first and second axial peripheral sections,
   wherein a rest plane is defined between the terminal ends of the first and second axial peripheral sections when said body is in said initial shape, and
   wherein the intermediate portion extends outside of said rest plane when said body is in said initial shape.

2. The implantable support of claim 1, where-in the intermediate section includes an apex extending between about 1 cm and about 5 cm above said rest plane.

3. The implantable support of claim 1, wherein the intermediate section includes an apex extending more than about 5 cm above said rest plane.

4. The implantable support of claim 1, wherein the intermediate section includes a mid location elevated in relation to a remainder of the intermediate section.

5. The implantable support of claim 1, wherein the intermediate section extends substantially an entire width of the support.

6. The implantable support of claim 1, wherein the intermediate section includes a depression extending downward back toward said rest plane.

7. The implantable support of claim 6, wherein the depression has a depth of between about 0.1 cm and about 1 cm relative to an apex where the intermediate section extends above said rest plane.

8. The implantable support of claim 6, wherein the depression extends downward through said rest plane.

9. The implantable support of claim 1, wherein the width of the body varies at different locations along a length of the body.

10. The implantable support of claim 9, wherein the width of the body varies by about 10% to about 50% relative to the width of the end of the body along the length of the body.

11. The implantable support of claim 9, wherein the width of the body at a first terminal end of the body is about equal to the width at a second terminal end of the body.

12. The implantable support of claim 9, wherein the width of the body at a first terminal end of the body is greater than the width at another location along the length of the body.

13. The implantable support of claim 1 wherein the terminal ends are notched across the width of the body.

14. The implantable support of claim 1 including one or more laterally extending projections located at each end of the semi-rigid body, and sized, shaped and oriented so as not to impede travel of the support into patient tissues and to impede travel of the support in a direction of removal from patient tissues.

15. The implantable device of claim 1 including one or more finger-engaging features located at terminal ends of the semi-rigid body for interfitting at least one of a finger of a medical operator and a shaft of a delivery device for assisting a medical operator in implanting the support device.

16. The implantable device of claim 1 including first and second arms extending from first and second hinge locations, respectively, at first and second terminal ends, respectively, of the semi-rigid body, the arms being lockable in place relative to the hinge locations.

17. A method for treating urinary incontinence comprising, making an incision in a vaginal wall of a patient, and inserting a semi-rigid body comprising a substantially uniform thickness sized and shaped for providing a urethral platform for treating urinary incontinence into a position under a urethra of a patient via the vaginal incision,
   wherein the body has an initial shape under rest conditions and is formed from a singular shape-resilient synthetic material, and is non-destructively, reversibly deformable in response to a mechanical forces associated with implantation of the device within a body of a patient,
   wherein the body has first and second axial peripheral sections having terminal ends and an intermediate portion between the first and second axial peripheral sections, and
   wherein a rest plane is defined between the terminal ends when the body is in said initial shape, and the intermediate portion extends outside of said rest plane when the body is in said initial shape.

* * * * *